(12) United States Patent
Pan et al.

(10) Patent No.: US 10,532,961 B2
(45) Date of Patent: Jan. 14, 2020

(54) CATALYST AND METHOD OF PREPARING LIGHT OLEFIN DIRECTLY FROM SYNTHESIS GAS BY ONE-STEP PROCESS

(71) Applicant: DALIAN INSTITUTE OF CHEMICAL PHYSICS, CHINESE ACADEMY OF SCIENCES, Dalian, Liaoning (CN)

(72) Inventors: Xiulian Pan, Liaoning (CN); Jinjing Li, Liaoning (CN); Feng Jiao, Liaoning (CN); Xinhe Bao, Liaoning (CN)

(73) Assignee: DALIAN INSTITUTE OF CHEMICAL PHYSICS, CHINESE ACADEMY OF SCIENCES, Dalian, Liaoning ( * ) Notice: Subject to any disclaimer, the term of this patent is extended or adjusted under 35 U.S.C. 154(b) by 0 days.

(21) Appl. No.: 15/740,653

(22) PCT Filed: Oct. 16, 2015

(86) PCT No.: PCT/CN2015/092091
§ 371 (c)(1),
(2) Date: Dec. 28, 2017

(87) PCT Pub. No.: WO2017/000427
PCT Pub. Date: Jan. 5, 2017

(65) Prior Publication Data
US 2018/0194700 A1    Jul. 12, 2018

(30) Foreign Application Priority Data
Jul. 2, 2015   (CN) .......................... 2015 1 0387209

(51) Int. Cl.
C07C 1/04    (2006.01)
B01J 23/06   (2006.01)
(Continued)

(52) U.S. Cl.
CPC ............. *C07C 1/0435* (2013.01); *B01J 23/06* (2013.01); *B01J 23/26* (2013.01); *B01J 23/34* (2013.01);
(Continued)

(58) Field of Classification Search
None
See application file for complete search history.

(56) References Cited

U.S. PATENT DOCUMENTS

2011/0033375 A1* 2/2011 Chaumonnot ........... B01J 20/18
                                                    423/701
2012/0000819 A1* 1/2012 Matsushita .......... B01J 29/7007
                                                   208/111.01
(Continued)

FOREIGN PATENT DOCUMENTS

CN    1067878 A    1/1993
CN    1083415 A    3/1994
(Continued)

OTHER PUBLICATIONS

Sun Hwan et al, Catalysts for direct production of light olefins from syngas and preparation method thereof, KR 100933062 machine translation, Dec. 21, 2009.*
(Continued)

*Primary Examiner* — Melvin C. Mayes
*Assistant Examiner* — Stefanie J Cohen
(74) *Attorney, Agent, or Firm* — Novick, Kim & Lee, PLLC; Allen Xue

(57) ABSTRACT

The present invention discloses catalyst and method for producing light olefins directly from synthesis gas by a one-step process, and particularly relates to method and catalyst for directly converting synthesis gas into light olefins by a one-step process. The provided catalysts are composite materials formed of multicomponent metal oxide
(Continued)

composites and inorganic solid acids with hierarchical pore structures. The inorganic solid acids have a hierarchical pore structure having micropores, mesopores and macropores. The metal composites can be mixed with or dispersed on surfaces or in pore channels of the inorganic solid acid and can catalyze the synthesis gas conversion to a $C_2$-$C_4$ light hydrocarbon product containing two to four carbon atoms. The single pass conversion of CO is 10%-60%. The selectivity of light hydrocarbon in all hydrocarbon products can be up to 60%-95%, wherein the selectivity of light olefins ($C_2^=$—$C_4^=$) is 50%-85%.

19 Claims, 4 Drawing Sheets

(51) Int. Cl.
| | |
|---|---|
| B01J 23/26 | (2006.01) |
| B01J 23/34 | (2006.01) |
| B01J 35/10 | (2006.01) |
| C07C 11/04 | (2006.01) |
| C07C 11/06 | (2006.01) |
| C07C 11/08 | (2006.01) |

(52) U.S. Cl.
CPC ............... *B01J 35/10* (2013.01); *C07C 11/04* (2013.01); *C07C 11/06* (2013.01); *C07C 11/08* (2013.01); *C10G 2400/20* (2013.01)

(56) References Cited

U.S. PATENT DOCUMENTS

| 2012/0219735 A1 | 8/2012 | Bakker et al. |
| 2014/0107371 A1 | 4/2014 | Bakker et al. |

FOREIGN PATENT DOCUMENTS

| CN | 101396662 A | 4/2009 |
| CN | 102219629 A | 10/2011 |
| CN | 103100415 A | 5/2013 |
| CN | 103979570 A | 8/2014 |
| CN | 104056627 A | 9/2014 |
| CN | 104307560 A | 1/2015 |
| EA | 007767 B1 | 12/2006 |
| EP | 1063013 A1 | 12/2000 |
| FR | 2571274 A1 | 4/1986 |
| JP | 2002284520 A | 10/2002 |
| JP | 2007181755 A | 7/2007 |
| RU | 2520218 C2 | 6/2014 |
| RU | 2524217 C2 | 7/2014 |
| WO | 2004060825 A1 | 7/2004 |
| WO | 2010116603 A1 | 10/2010 |
| WO | 2011077955 A1 | 6/2011 |

OTHER PUBLICATIONS

Dubinin, surface and porosity adsorbents, translated from Uspekhi Khmi, 51, 1065-1074 (Year: 1982).*
Xueping Yang et al., "Technical progress and economical ananysis on the direct production of light olefins from syngas", Chemical Industry and Engineering Progress, 2012, vol. 31, No. 8, pp. 1726-1731.
Jingchang Zhang et al, "Prepareation and Characterization of Fe/AC Catalysts for Synthesis of Light Olefins via Carbon Monoxide Hydrogenation", Chinese Journal of Catalysis, Apr. 2003, vol. 24, No. 4, pp. 259-264.
Hirsa M. Torres Galvis et al., "Effects of sodium and sulfur on catalytic performance of supported iron catalysts for the Fischer-Tropsch synthesis of lower olefins", Journal of Catalysis, 2013, vol. 303, pp. 22-30.
Jianyi Shen et al., "Studies on Highly Dispersed Iron/Activated Carbon Catalysts for Fischer-Tropsch Synthesis", Journal of Fuel Chemistry and Technology, Dec. 1991, vol. 19, No. 4, pp. 289-297.
Jo-Yong Park et al., "Direct conversion of synthesis gas to light olefins using dual bed reactor", Journal of Industrial and Engineering Chemistry, 2009, vol. 15, pp. 847-853.
Mingting Xu et al., "Synthesis of dimethyl ether(DME) from methanol over solid-acid catalysts", Applied Catalysis A: General, 1997, vol. 149, pp. 289-301.
Javier Erna et al., "Conversion of syngas to liquid hydrocarbons over a two-component (Cr2O3—ZnO and ZSM—5 zeolite) catalyst: Kinetic modelling and catalyst deactivation", Chemical Engineering Science, 2000, vol. 55,pp. 1845-1855.
Javier Erna et al., "Study of the preparation and composition of the metallic function for the selective hydrogenation of CO2 to gasoline over bifunctional catalysts", Chem Technol Biotechnol, 78:161-166 (online: 2003).
Dongsen Mao et al., "Highly effective hybrid catalyst for the direct synthesis of dimethyl ether from syngas with magnesium oxide-modified HZSM—5 as a dehydration component", Journal of Catalysis, 230 (2005) 140-149.
Wenping Ma et al., "Non-Aderson-Schulz-Flory Product Distribution of Fischer-Tropsch Synthesis over Iron/Ativated Charcoal Catalyst", Chinese Journal of Catalysis, May 2001, vol. 22, No. 3.
D. Chen et al.; A methanol to olefins review: Diffusion, coke formation and deactivation on SAPO type catalysts; Microporous and Mesoporous Materials 164 (2012) 239-250.
Guohui Yang et al.; Confinement Effect and Synergistic Function of H—ZSM—5/Cu—ZnO—Al2O3 Capsule Catalyst for One-Step Controlled Synthesis; JACS Articles Published on Web May 19, 2010.
R A Friedel et al.; Composition of Synthetic Liquid Fuels. I. Product Distribution and Analysis of C5—C8 Paraffin Isomers from Cobalt Catalyst; 72, 1212 (1950).
Kaoru Fujimoto et al; Synthesis Gas Conversion Utilizing Mixed Catalyst Composed of CO Reducing Catalyst and Solid Acid IV. Selective Synthesis of C2, C3, and C4 Paraffins from Synthesis Gas; Journal of Catalysis 94, 16-23 (1985).
Qingjie Ge et al.; Direct synthesis of LPG from synthesis gas over Pd—Zn—Cr/Pd-beta hybrid catalysts; Journal of Molecular Catalysis A: Chemical 278 (2007) 215-219.
Zhong-Wen Liu et al.; Iso-paraffins synthesis from modified Fischer-Tropsch reaction—Insights into Pd/beta and Pt/beta catalysts; Catalysis Today 104 (2005) 41-47.
Pravakar Mohanty et al.; Liquid fuel production from syngas using bifunctional CuO—CoO—Cr2O3 catalyst mixed with MFI zeolite; Fuel Processing Technology 92 (2011) 600-608.
Gerome Melaet et al.; Evidence of Highly Active Cobalt Oxide Catalyst for the Fischer-Tropsch Synthesis and CO2 Hydrogenation; Journal of the American Chemical Society 2014, 136, 2260-2263.
Ruud Snel; Olefins from Syngas; Catalysis Reviews Science and Engineering 29:4, pp. 361-445.
Javier Erena et al.; Study of Physical Mixtures of Cr2O3—ZnO and ZSM—5 Catalysts for the Transformation of Syngas into Liquid Hydrocarbons; Ind. Eng. Chem. Res. 1998, 37, pp. 1211-1219.
Yutaka Tamaura et al.; Complete reduction of carbon dioxide to carbon using cation-excess magnetite; Nature, vol. 346, Jul. 19, 1990.
Hirsa M Torres Galvis et al.; Supported Iron Nanoparticles as Catalysts for Sustainable Production of Lower Olefins; Science, vol. 335, Feb. 17, 2012, pp. 835-838.
Hirsa M Torres Galvis et al.; Catalysts for Production of Lower Olefins from Synthesis Gas: A Review; American Chemical Society Catal. 2013, 3, pp. 2130-2149.
Yingying Yu et al; Transformation of syngas to light hydrocarbons over bifunctional CuO—ZnO/SAPO—34 catalysts: the effect of preparation methods; Reac Kinet Mech Cat (2014) 112, pp. 489-497.
Xu-Yide et al.; A new supported Fe-MnO catalyst for the production of light olefins from syngas. II. Effect of support on the secondary reactions of C2H4; Catalysis Letters 24 (1994), pp. 187-195.

(56) References Cited

OTHER PUBLICATIONS

Qihang Lin et al. "Design of a Hierarchical Meso/Macroporous Zeolite-Supported Cobalt Catalyst for the Enhanced Directt Synethesis of Isoparaffins from Syngas" Chemcatchem, Jan. 30, 2015, pp. 682-689, vol. 7, No. 4, ISSN:1867-3880, DOI:10.1002/CCTC.201402929.

Ming-Hui Sun et al. "A comparative study of hierarchically micro-meso-macroporous solid-acid catalysts constructed by zeolites nanocrystals synthesized via a quasi-solid-state crystallization process" Microporous and Mesoprous Materials, Sep. 2013, pp. 122-135, vol. 182, Wuhan, China ISSN: 1387-18811, doi:10.1016/j.Micromeso.2013.08.034.

* cited by examiner

CATALYST AND METHOD OF PREPARING LIGHT OLEFIN DIRECTLY FROM SYNTHESIS GAS BY ONE-STEP PROCESS

TECHNICAL FIELD

The present invention belongs to the field of preparation for light olefins, and particularly relates to a method for preparing light olefins from synthesis gas by a one-step process and a catalyst.

BACKGROUND

Light olefins include ethylene, propylene and butene, and are important raw materials for synthesizing plastics, fibers and various chemical materials. With the growth of the national economy, the consumption of and demand for the light olefins are increasing rapidly. At present, the light olefins are produced mainly via the petrochemical route by naphtha cracking. With the decreasing global oil resources and the high price of crude oil, for countries especially like China with a shortage of oil resources, more than 60% of the consumed oil relies on imports every year. 70% of raw material for producing the light olefins comes from naphtha and light hydrocarbons obtained by refining crude oil in China. It is of important social significance and strategic significance to seek an alternative technological route from non-oil-based carbon resources such as coal, biomass and the like, for production of light olefins.

China has rich coal resources. Coal is used as the raw material and gasified to obtain synthesis gas (i.e., mixed gas of CO and $H_2$); and the synthesis gas can be converted to methanol. The technology for production of olefins from methanol, i.e. methanol-to-olefins (MTO) is mature and is already industrialized. The catalyst is based on molecular sieves such as SAPO-34 or ZSM-5. The methanol conversion can reach close to 100%, and the selectivity of ethylene and propylene is 85% to 90%. Only a small amount of long-carbon-chain hydrocarbons (above $C_{5+}$) are generated. In August 2010, the world's first commercial plant based on the DMTO technology developed by Dalian Institute of Chemical Physics (DICP) with independently intellectual property rights realizes commercial operation, representing a milestone progress in the emerging industries of producing olefins from coal in China. In April 2015, another 600k ton/year scale MTO plant was set up at Zhejiang Xingxing New Energy Co. Ltd., which also uses the core technology of DICP. It is the eighth set of large-scale industrial plant for production of olefins from coal-based methanol in China.

Compared with the indirect route of light olefins synthesis from coal-synthesis gas-methanol-light olefins, a direct synthesis route from synthesis gas by one-step process would make the process much simpler, much shorter process flow, much lower capital investment and production cost. To achieve direct conversion of synthesis gas to light olefins by one-step process, researchers from academia and industry have invested a great number of resources and efforts, studying on direct conversion of synthesis gas to light olefins. Sinopec Shanghai Research Institute of Petrochemical Technology, carried out economical assessment of the direct conversion technology based on the conventional Fischer-Tropsch technology from coal-based synthesis gas [Yang Xueping, Dong Li. Progress in Chemical Engineering 31 (2012) 1726-1731], named as FTTO technology in this patent. The FTTO technology had advantages in the selling cost when the oil price was $110/Barrel, coal price was not higher than RMB 520/ton, and the olefins concentration in all products was 30%. If the light olefins concentration in all products was higher than 40%, the economic advantage of the FTTO technology will become more advantageous.

Direct conversion of synthesis gas to light olefins can be achieved via the traditional Fischer-Tropsch synthesis route. In that process, metal and metal carbides are used as catalysts. CO is generally considered to adsorb and dissociate on the surface of the catalyst and is hydrogenated to generate $CH_x$ intermediate species on the surface. These surface CHx intermediates go through polymerization on the catalyst surface, growing into longer carbon chain hydrocarbons, thereby forming hydrocarbons with a wide range of carbon numbers. Therefore, the process involves a series of elemental reactions, such as C—O bond breaking, C—H bond formation (i.e. hydrogenation), and C—C coupling. Typical product distribution follows the Anderson-Schultz-Flory (ASF) distribution model, which can be expressed as $\ln(W_n/n)=n\ln P+\ln[(1-P)2/P]$, wherein Wn means the mass percent of hydrocarbon containing n carbon atoms, P means the chain growth probability, and (1−P) means the chain end probability. Polymerization degree D equals $1/(1-P)$. Once P is determined, the entire product distribution is determined. The characteristics of Fischer-Tropsch process is a wide distribution of hydrocarbons with different carbon atom numbers. For example, the selectivity of $C_2$-$C_4$ hydrocarbon is no more than 58%, while the highest selectivity of gasoline fraction ($C_5$-$C_{11}$) is 45%. In the meanwhile, a large amount of methane and higher alkane are generated. How to achieve selective synthesis of light olefins directly from synthesis gas remains a challenge since Fischer-Tropsch synthesis technology was invented. Researchers from all over the world have made a great deal of efforts, taking a variety of measures trying to improve the selectivity of light olefins, for example, by modifying the catalyst structures and compositions, in order to modify the reaction rates of different elemental steps in the process, such as methanation, hydrogenation, secondary reaction of light olefins, carbon chain growth and the like.

Fe-based catalysts have the advantages of low cost, easy availability, high activity, high selectivity of light olefins and the like, and were considered to be the most promising catalysts for synthesis of light olefin directly from synthesis gas. Researchers consequently have improved the selectivity of light olefins by adding additives with different components such as alkali metal K, Na and their salts, and transition metals such as Mn, Cu. Ruhr Chemical Corporation of Germany developed an iron-based catalyst promoted with multi-components Fe—Zn—Mn—K, which can catalyze direct conversion of synthesis gas to light olefins. Jingchang Zhang et al. from Beijing University of Chemical Technology reported a Fe—Mn—K/AC catalyst prepared using ferric oxalate as the precursor. That catalyst gave a CO conversion as high as 97% at a space velocity of 600 $h^{-1}$, 15 bars and 320° C.; and the selectivity of $C_2^=$-$C_4^=$ in hydrocarbons was 68% (excluding CO2) [Zhang Jingchang, Wei Guobin, Cao Weiliang, Chinese Journal of Catalysis 24(2003)259-264], which exceeded the selectivity limit of $C_2$-$C_4$ hydrocarbons predicted by the ASF distribution model.

The studies showed that the catalyst support materials also has a very important modification role in the product selectivity through interaction with Fe species. The research group of Professor de Jong reported a 12 wt % Fe catalyst supported on carbon nanofiber (CNF) and a-$Al_2O_3$ using ferric ammonium citrate as the precursor. Under reaction conditions of low pressure (1 bar), 350° C. and $H_2$/CO=1, at a reaction time of 15 hours, the CO conversion was 0.5%-

1.0% and the selectivity of light olefins among hydrocarbons was 60% [H. M. T. Galvis, J. H. Bitter, C. B. Hhare, M. Ruitenbeek, A. L. Dugulan, K. P. de Jong, Science 335 (2012) 835-838]. The same catalyst under conditions of 340° C., $H_2/CO=1$, 20 bars and space velocity of 1500 $h^{-1}$, a CO conversion of 70%-88% was obtained. The space time yield was $2.98 \times 10^{-5}$ mol CO/gFe·s and $1.35 \times 10^{-5}$ mol CO/gFe·s, respectively. The selectivity of $CO_2$ was 42%-46%, and the selectivity of light olefins among all hydrocarbons was 52%-53%. Later, they reported that a small amount of 0.03% of S and about 0.2% of Na added into the catalyst improved obviously the activity and the selectivity of the light olefins [H. M. T. Galvis, A. C. J. Koeken, J. H. Bitter, T. Davidian, M. Ruitenbeek, A. I. Dugulan, K. P. de Jong, J. Catal. 303 (2013) 22-30]. The researchers from Dalian Institute of Chemical Physics of the Chinese Academy of Sciences studied systematically the effects of activated carbon as the support. They found that the products on the activated carbon supported iron catalysts deviated from the ASF distribution model [Shen Jianyi, Lin Liwu, Zhang Su, and Liang dongBai, Journal of Fuel Chemistry and Technology 19 (1991) 289-297; Ma Wenping, Ding Yunjie, Luo Hongyuan, et al., Chinese Journal of Catalysis, 22 (2001) 279-282]. In addition, the catalyst preparation methods and conditions, such as the conditions of the calcination and reduction processes, can also affect directly the dispersion and the size of active species, thereby changing the catalytic activity and the product selectivity. The researchers from Beijing University of Chemical Technology prepared a nano-sized Fe-based catalyst by using a supercritical fluid technology combining with chemical precipitation, gelation, and supercritical drying methods, which led to a highly dispersed iron catalyst. With that catalyst, a CO conversion higher than 96% and the selectivity of light olefins among hydrocarbons higher than 54% were reported [Beijing University of Chemical Technology; A nano catalyst for preparing light olefins from synthesis gas and a preparation method: China, 101396662 [P]2009-04-01].

Other strategies, for instance combining Fischer-Tropsch synthesis with other reactions such as cracking reactions in a double-bed reactor were also reported [J. L. Park, Y J. Lee, K. ff Jun, J. ff Bae, N. Vi swanadham, Y H. Kim, J. Ind. Eng. Chem. 15 (2009) 847-853]. In the first reactor, the Fischer-Tropsch reaction was carried over Fe—Cu—Al catalyst under conditions of 300° C., 10 atm and GHSV=3600 $h^{-1}$. Then, the effluents were passed through the second reactor at 500° C. where the cracking catalyst of ZSM-5 was packed. In that way, much $C_{5+}$ products were cracked to light olefins. Thus a selectivity of light olefins among hydrocarbons was 52%, and the selectivity of the light olefins in total products was 28%.

In comparison, the technology of synthesis gas to methanol and then methanol to olefins is mature and commercialized. Therefore, there were also a lot of attempts of combining these two processes. For example, Xu et al. mixed CuO—ZnO—$Al_2O_3$ with ZSM-5 to obtain a catalyst, however, it gave mainly dimethyl ether as the product in synthesis gas conversion [M. Xu, J. H. Lunsford, D. ff Goodman, A. Bhattacharyya, Appl. Catal. A. General 149 (1997) 289; D. Mao, if Yang, J. Xia, B. Zhang, Q. Song, Q. Chen, J. Catal. 230 (2005) 140]. Erena et al. mixed multicomponent metal composites such as $CuO/ZnO/Al_2O_3$ and the like with ZSM-5 molecular sieves to catalyze the conversion of synthesis gas. However, the products were mainly gasoline [J. Erena, J. M. Arandes, J. Bilbao, A. G Gayubo, H. I. De Lasa, Chemical Engineering Science 2000, 55, 1845; J. Erena, J. M. Arandes, R. Garona, A. G Gayubo, J. Bilbao, Journal of Chemical Technology and Biotechnology 2003, 78, 161].

The present invention provides a method and catalyst for directly converting synthesis gas for production of light olefins. The selectivity of the hydrocarbon products containing 2-4 carbon atoms is up to 60%-95%, and the selectivity of light olefins including ethylene, propylene and butane is 50%-85%.

SUMMARY

In view of the above problems, the present invention provides a method and catalyst for directly converting synthesis gas for production of light olefins within a one-step process. In the method, through a composite catalyst material, CO molecule is activated on a metal composite surface defects. Another CO reacts with the dissociated oxygen atom to form $CO_2$. Thus, the oxygen in the CO molecule is removed directly by CO molecules instead of hydrogen while forming hydrocarbon products, which avoids consumption of extra high-value hydrogen. In this way, a synthesis gas with a low H/C ratio can be used as the feed directly, such as a ratio of H/C=0.5. Thus, the synthesis gas from a coal gasifier can be utilized directly in this invented technology. Thus, the energy-intensive and water-intensive water-gas shift process to produce extra hydrogen for modulating the H/C ratio in the synthesis gas can be discarded.

On the other hand, the $CH_x$ intermediates generated on the composite surface do not adsorb strongly on the composite surface. They will desorb into the gas phase. When they land on the active sites within the pore channels of molecule sieves, they go through C—C coupling within the confined channels where they grow into desired hydrocarbon products. Target hydrocarbon molecules are selectively generated, thereby achieving the one-step direct catalytic conversion of synthesis gas and generating light olefins with a high selectivity. This process not only gives a selectivity beyond the limit predicted by the ASF distribution model in the traditional Fischer-Tropsch synthesis, but also abandons additional methanol synthesis process and water-gas shift process. The selectivity of light olefins in hydrocarbons is as high as 50%-85%, and a single pass CO conversion is 10%-50%. The method has the characteristics of simpler process, less operation units, shorter process flow and lower capital investment, in addition to a much higher selectivity to the desired products. It is anticipated that the method can obviously reduce the production cost of the light olefins from coal and has important application potentials.

The present invention provides the technical solutions:

The catalyst is a composite material composed of multi-component metal composites and inorganic solid acid with hierarchical pore structures. The inorganic solid acid has a hierarchical pore structure having micropores, mesopores and macropores. The metal composites are dispersed on surfaces or in pore channels of the inorganic solid acid.

The content of the multicomponent metal oxide composites in the whole catalyst is 10 wt % to 75 wt % of total weight (100%) of the catalyst, and preferably 25 wt % to 75 wt %.

The inorganic solid acid with hierarchical pore structures is composed of secondary particles of the inorganic solid acid. The size of the secondary particles of the inorganic solid acid is 100 nm to 500 μm, and preferably 150 nm to 100 μm.

The secondary particles of the inorganic solid acid are formed by stacking inorganic solid acid crystal particles with a size of 5 to 200 nm (preferably 20 nm to 120 nm).

The secondary particles of the inorganic solid acid have a three-dimensional pore channel with a hierarchical structure, including three kinds of pore channels of primary pores, secondary pores and tertiary pores.

The primary pores are micropore channels with a diameter less than 2 nm. Micropores are located in the inorganic solid acid crystal particles. The secondary pores are mesopore channels with a diameter of 2 nm to 50 nm and preferably 2 nm to 15 nm. The secondary pores are formed by the stacked inorganic solid acid crystals. The secondary pores are located in the secondary particles of the inorganic solid acid and in the pore walls of the tertiary pores.

The tertiary pores are macropore channels with a diameter distribution greater than 50 nm. The tertiary pores are formed by stacking the secondary particles of the inorganic solid acid.

The three kinds of pore channels are connected and communicated with each other to form the three-dimensional hierarchical pore structure. The secondary pores can be located in pore walls of adjacent tertiary pores. The primary pores can be located in the walls of adjacent secondary pores and/or tertiary pores.

The BET specific surface area of the inorganic solid acid with the hierarchical pore structure determined by $N_2$ physical adsorption is 100-1200 $m^2/g$, and pore volume is 0.25-0.80 ml/g. Through calculation according to the specific surface area, microporous specific surface area occupies 10-65%, mesoporous specific surface area occupies 20-75%, and macroporous specific surface area occupies 15-70%. Preferably, the microporous specific surface area occupies 10-60%, the mesoporous specific surface area occupies 20-70%, and the macroporous specific surface area occupies 20-70%. More preferably, the microporous specific surface area occupies 10-50%, the mesoporous specific surface area occupies 30-70%, and the macroporous specific surface area occupies 20-60%.

The metal in the multicomponent metal composite comprises two or more than three kinds of metal elements, and preferably two to five kinds of metal elements. The metal composite comprises one or more than two of metal oxides, metals, metal carbides, metal nitrides and metal inorganic acid salts.

The metal elements comprise necessary metal elements and other elements, wherein the necessary metal elements are Zn or Co or Cr or Mn.

If the necessary metal element is Zn, other elements are one or more than two of Li, Na, Mg, Al, K, Ca, Sr, Ba, Ti, V, Cr, Mn, Fe, Co, Cu, Ga, Ge, Zr, Mo, Pd, Ag, Cd, In, Sn, Cs, La and Ce. Preferably, other elements are one or more than two of Al, K, Ti, V, Cr, Mn, Co, Cu, Ce and Pd. More preferably, other elements are one or more than two of Al, Ti, Cr, Mn, Co, Cu, Pd and Ce.

If the necessary metal element is Co, other elements are one or more than two of Li, Na, Mg Al, K, Ca, Sr, Ba, Ti, V, Cr, Mn, Fe, Cu, Zn, Ga, Ge, Zr, Mo, Pd, Ag, Cd, In, Sn, Cs, La and Ce. Preferably, other elements are one or more than two of Al, K, Ti, V, Cr, Mn, Cu, Zn, Ce and Pd. More preferably, other elements are one or more than two of Al, Ti, Cr, Mn, Cu, Zn, Pd and Ce.

If the necessary metal element is Cr, other elements are one or more than two of Li, Na, Mg, Al, K, Ca, Sr, Ba, Ti, V, Mn, Fe, Co, Cu, Zn, Ga, Ge, Zr, Mo, Pd, Ag, Cd, In, Sn, Cs, La and Ce. Preferably, other elements are one or more than two of Al, K, Ti, V, Mn, Co, Cu, Zn, Ce and Pd. More preferably, other elements are one or more than two of Al, Ti, Mn, Co, Cu, Zn, Pd and Ce.

If the necessary metal element is Mn, other elements are one or more than two of Li, Na, Mg, Al, K, Ca, Sr, Ba, Ti, Cr, Fe, Co, Cu, Zn, Ga, Ge, Zr, Mo, Pd, Ag, Cd, In, Sn, Cs, La and Ce. Preferably, other elements are one or more than two of Al, K, Ti, V, Cr, Co, Cu, Zn, In, La, Mo, Ce and Pd. More preferably, other elements are one or more than two of Al, Ti, Cr, Co, Cu, Zn, Pd and Ce.

In the multicomponent metal composites, the content of the metal oxides is 5-90%. The total mass content of one or more than two of metals, metal carbides and metal nitrides can be less than or equal to 10%. The content of metal inorganic acid salts is 10-95%. Preferably, the content of the metal oxide is 30-90%, the total mass content of one or more than two of metals, metal carbides and metal nitrides is less than 5% and the content of the metal inorganic acid salts is 10-70%.

The total molar ratio of necessary element Zn or Co or Cr or Mn to other elements in the multicomponent metal composites is (0.1-5.0):1, and preferably, (0.2-3.5):1.

The inorganic acid salt is composed of cations and anions, wherein one or more than two of Li, Na, Mg, Al, K, Ca, Sr, Ba, Ti, V, Cr, Mn, Fe, Co, Cu, Zn, Ga, Ge, Zr, Mo, Pd, Ag, Cd, Sn, Cs and Ce can exist in the form of cations, while Al, Si, V, Cr, Mn, Fe, Co, Zn, Mo, Ti, Zr, Ce, Ga, In and Ge can also exist in one or more than two forms of anions like $ZnO_2^{2-}$, $Al_2O_4^{2-}$, $SiO_3^{2-}$, $SiO_4^{4-}$, $TiO_3^{2-}$, $TiO_3^{3-}$, $VO_{3-}$, $VO_3^{2-}$, $CrO_4^{2-}$, $Cr_2O_4^{2-}$, $Mn_2O_4^{2-}$, $Fe_2O_4^{2-}$, $CO_2O_4^{2-}$, $Ni_2O_4^{2-}$, $Fe(CN)_6^{3-}$, $Fe(CN)_6^{4-}$, $MoO_4^{2-}$, $TiO_3^{2-}$, $ZrO_3^{2-}$, $CeO_3^{2-}$, $Ga_2O_4^{2-}$, $In_2O_4^{2-}$, $GeO_3^{2-}$, $GeO_4^{4-}$ and $SrO_3^{4-}$. The cations and the anions form the inorganic acid salts. The compositions of the inorganic acid salts are listed in Table 1. Metal elements that compose the cations and the anions are different.

The metal composite is formed by uniformly dispersing crystal particles of one or more than two of metal oxides, metals, metal carbides, metal nitrides and metal inorganic acid salts in claim 2. The size of the crystal particles is 0.5-20 nm, and preferably 1-10 nm. Meanwhile, the crystal particles are further stacked into secondary particles. The size of the secondary particle is 10 nm-200 μm. The diameter of pore channels formed by stacking the crystal particles in the secondary particles is 2-20 nm, and preferably 5-15 nm.

The inorganic solid acid is composed of H and O as necessary elements and one or more than two elements of Al, Si, P, Zr, Ti and Ge to form one or more than two of inorganic solid acids composed of Si, O and H elements, inorganic solid acids composed of Si, Al, O and H elements, inorganic solid acids composed of Si, Al, P, O and H elements, inorganic solid acids composed of Ti, Si, O and H elements, inorganic solid acids composed of Zr, Si, O and H elements, inorganic solid acids composed of Ge, Si, O and H elements and inorganic solid acids composed of Ge, Al, P, O and H elements.

The inorganic solid acids with hierarchical pore structures has acid features.

The acid sites are distributed in the three-dimensional hierarchical pore channels in claim 1.

According to the acid intensity defined by $NH_3$-TPD (temperature programmed desorption), the inorganic solid acids contain three kinds of acid sites: weak acid sites, medium strong acid sites and strong acid sites.

The $NH_3$-TPD records the desorption position of $NH_3$. The position of the desorption peak means that under standard test conditions that a ratio of sample mass w and carrier gas flow rate f (w/f) is 100 g·h/L and a heating rate is 10° C./min, a TCD records a thermal conductivity signal of desorption of $NH_3$ and draws a desorption curve; according to the peak positions of the curve (the temperature where the peak reaches a maximum point), the inorganic solids can be categorized into three acid intensities.

The weak acid is an acid site where the deposition temperature of $NH_3$ is lower than 275° C.

The medium strong acid is an acid site where the deposition temperature of $NH_3$ is between 275° C. and 500° C.

The strong acid is an acid site where the deposition temperature of $NH_3$ is higher than 500° C.

In the inorganic solid acid, the amount of the medium strong acid site is 0.06-10 mol/kg, and preferably 1-10 mol/kg.

The multicomponent metal composite and the inorganic solid acid with a hierarchical pore structure form the composite material. The particles with a size of 0.5-10 nm in the multicomponent metal composite can be located in the pore channels of micropores, mesopores or macropores of the inorganic solid acid or with hierarchical pore structure and on the external surface of the inorganic solid acid. The secondary particles with a size of 10-200 nm in the multicomponent metal composite can be located in the pore channels of macropores and mesopore of the inorganic solid acid with hierarchical pore structure or on the external surface of the inorganic solid acid. The secondary particles with a size greater than 200 nm in the multicomponent metal composite are dispersed on the external surface of the inorganic solid acid with hierarchical pore structures. The external surface of the multicomponent metal composite, the internal surfaces of macropores and mesopores of the inorganic solid acid, and the external surfaces of the secondary particles of the inorganic solid acid are stacked to form active pores. The active pores are connected with the mesopores of the metal composite and three-dimensional three-level pore channels in the inorganic solid acid with hierarchical pore structure, so that all the pore channels are communicated and compounded.

The preparation method of the inorganic solid acid with hierarchical pore structure includes a soft template hydrothermal method, a hard template hydrothermal method or a crystallization controlled hydrothermal method. In the aging operation of the soft template hydrothermal method, the hard template hydrothermal method or the crystallization controlled hydrothermal method, constant temperature stirring and aging treatment is beneficial to forming the inorganic solid acid with hierarchical pore structure.

The crystallization controlled hydrothermal method includes rapid aging and control of stirring rate and temperature in a crystallization process to avoid the excessive growth of crystal particles of a molecular sieve and promote the formation of small crystal particles, so as to generate intercrystalline mesopores among more small crystal particles, thereby obtaining the inorganic solid acid with hierarchical pore structure. Meanwhile, the conditions of aging and crystallization are regulated to regulate the acid intensity and the amount of the medium strong acid in claim 5. Specific steps comprise: preparation of homogeneous sol dispersion liquid, aging, crystallization, washing, drying and calcination. The preparation of the homogeneous sol dispersion liquid includes: weighing precursors of elements included in the inorganic solid acid according to a required proportion and then putting the precursors into a container with water, stirring and dispersing at room temperature, and simultaneously adding an organic microporous template agent to prepare a liquid phase dispersion system. The aging method includes: controlling the prepared liquid phase dispersion system at a temperature of 20-60° C., a time of 10 min-24 h and a stirring speed of 50-1000 rpm. In the crystallization process, the stirring speed is 50-500 rpm, the temperature is 120-250° C. and the time is 12 h-10 d. The washing method may be filtration washing or centrifugal washing. In the filtration washing, pH of filter liquor should be 6.5-7.5 at the end of washing. In the centrifugal washing, pH of supernatant should be 6.5-7.5 at the end of washing. In the drying process, the temperature is 100-150° C. and the time is longer than 12 h. In the calcination process, the temperature is 500-650° C. and the time is 1-8 h.

The soft template hydrothermal method refers to synthesizing the inorganic solid acid with hierarchical pore structure through a hydrothermal method by using an organic mesoporous template agent. Specific steps involve preparation of the homogeneous sol dispersion liquid, aging, crystallization, washing, drying and calcination. The preparation of the homogeneous sol dispersion liquid includes: weighing precursors of elements included in the inorganic solid acid according to a required proportion and then putting the precursors into a container with water, stirring and dispersing at room temperature, and simultaneously adding an organic microporous template agent and an organic mesoporous template agent (with a mass ratio of 0.3-0.8) to prepare a liquid phase dispersion system. In the aging process, the temperature is controlled as 20-60° C., the time is controlled as 10 min-24 h and the stirring speed is controlled as 50-1000 rpm. In the crystallization process, the stirring speed is 50-500 rpm, the temperature is 120-250° C. and the time is 12 h-10 d. The washing method may be filtration washing or centrifugal washing. In the filtration washing, pH of filter liquor should be 6.5-7.5 at the end of washing. In the centrifugal washing, pH of supernatant should be 6.5-7.5 at the end of washing. In the drying process, the temperature is 100-150° C. and the time is longer than 12 h. In the calcination process, the temperature is 500-650° C. and the time is 1-8 h.

The hard template hydrothermal method refers to synthesizing the inorganic solid acid with hierarchical pore structure through a hydrothermal method by using one of more than two of carbon nanomaterial that can be oxidized at 650° C., SBA series, M41S series, HMS series, MSU series, KIT series, FDU series, AMS series, HMO series and MCM-41 mesoporous molecular sieve as hard templates. Specific steps involve preparation of the homogeneous sol dispersion liquid, aging, crystallization, washing, drying and calcination. The preparation of the homogeneous sol dispersion liquid includes: weighing precursors of elements included in the inorganic solid acid according to a required proportion and then putting the precursors into a container with water, stirring and dispersing, and simultaneously adding an organic microporous template agent and hard template material (with a mass ratio of 0.3-0.8) to prepare a liquid phase dispersion system. The growth of the crystal particles is suppressed to promote small crystal particles to form mesopores. The temperature is controlled as 20-60° C., the time is controlled as 10 min-24 h and the stirring speed is controlled as 50-1000 rpm. In the crystallization process, the stirring speed is 50-500 rpm, the temperature is 120-250° C. and the time is 12 h-10 d. The washing method may be filtration washing or centrifugal washing. In the filtration washing, pH of filter liquor should be 6.5-7.5 at the end of washing. In the centrifugal washing, pH of supernatant should be 6.5-7.5 at the end of washing. In the drying process, the temperature is 100-150° C. and the time is longer than 12 h. In the calcination process, the temperature is 500-700° C. and the time is 1-8 h.

The precursor in the homogeneous sol dispersion liquid is one or more than two of water glass, silica sol, ultramicro $SiO_2$, white carbon black, sodium silicate, TMOS, silicate ester, tetrachlorosilane, kaolin, aluminum nitrate, aluminum sulfate, sodium aluminate, boehmite, pseudo boehmite, gibbsite, aluminum isopropoxide trihydrate, alchlor, aluminium hydroxide, alkoxy aluminum, ultrafine powder aluminum, alumina, phosphoric acid, aluminum phosphate, sodium phosphate, zirconium oxide, zirconium nitrate, zirconium phosphate, zirconium silicate, titanium tetrachloride, butyl titanate, titanium oxide, germanium oxide, germanium nitrate, germanium chloride, methyltrichlorogermane and tetraethylgermanium.

The organic microporous template agent is one or more than two of TMA, TPA, TEA, TEAOH, DDO, TBA, TQA, ethylenediamine, pyrrolidine, choline, PDN, RDN, PDA, pentaerythritol, hydroxy acid, propyl sulfaldehyde, tripropyl amine, DABCO, dipropylamine, tert-butylamine, isopropylamine, quinuclidine, neopentylamine, triethanolamine, dicyclohexylamine, N,N-dimethyl-benzylamine, N,N-dimethyl hydramine, N,N-dimethylethanolamine, 2-picoline, piperidine and morphine.

The organic mesoporous template agent is one of more than two of CTBA, CTBABr, monododecyl phosphate, long-chain primary amine, polyethylene oxide, polypropylene oxide, polyoxyethylene block ether copolymer, P123, crosslinking agent of gelatin and glutaral, and TPHAC.

The mass ratio of the sol precursors to the organic template agents (including the organic microporous template agent and the organic mesoporous template agent) to water is: sol precursors:organic template agents: water=(20-65):(15-50):100.

The compounding mode of the multicomponent metal composite and the inorganic solid acid with hierarchical pore structure in the catalyst includes a coating growth method, an ultrasonic assisted chemical compounding method or a physical compounding method.

The coating growth method refers to growing a layer of inorganic solid acid with a hierarchical pore structure, with a coverage rate of at least above 80% or 100% on the surface of the multicomponent metal composite through the method in claim 6, i.e., firstly preparing the homogeneous sol dispersion liquid, uniformly dispersing the multicomponent metal composite in the homogeneous sol dispersion liquid, and conducting aging, crystallization, washing, drying and calcination to obtain the multicomponent metal composite coated with the inorganic solid acid with hierarchical pore structure. In the multicomponent metal composite, the metal oxide and the inorganic acid salt composed of Mg, Al, Ca, Sr, Ba, Ti, V, Cr, Mn, Fe, Co, Cu, Zn, Zr, Mo, Pd, Ag, Cd, In, Sn, La and Ce elements are prepared by a co-precipitation method, an impregnation method or an ultrasonic ion-exchange method. The metal oxide and the inorganic acid salt composed of Li, Na, K, Ga, Ge and Cs elements are prepared by an impregnation method or an ultrasonic ion-exchange method. The metal oxide and the inorganic acid salt composed of Al, Fe, Co, Cu, Zn, Mo and Pd elements can also be prepared by a chemical vapor deposition method or an impregnation method.

The ultrasonic assisted chemical compounding method refers to introducing and compounding the multicomponent metal composite to the inorganic solid acid with hierarchical pore structure through the ultrasonic co-precipitation method, the chemical vapor deposition method or the ultrasonic ion-exchange method.

The physical compounding method refers to compounding the inorganic solid acid with hierarchical pore structure and the multicomponent metal composite through methods such as ball milling, a mechanical mixing method, a shaker and shocker oscillating mixing.

The ultrasonic co-precipitation method includes dissolving two or more than three of metal precursors required by the multicomponent metal composite in a solvent to obtain two or more than three of metal cation solutions and then adding the inorganic solid acid with hierarchical pore structure into the solution under ultrasonic agitation conditions. The ultrasonic method could be bath ultrasonic or tip ultrasonic method. The ultrasonic power is 1-20 W/(ml sample), and the frequency is 40 KHz-80 MHz. Precipitation temperature is 2-80° C., time is 2 min-2 h and the stirring rate is 50-1000 rpm. After mixing uniformly, a precipitant is added according to a required mass ratio to obtain a homogeneous precipitate, and the precipitate is dried and calcined. Drying temperature is 80-150° C. and time is longer than 12 h. Calcination temperature is 300-650° C. and time is 1-3 h.

In the ultrasonic co-precipitation method, the metal precursor is selected from one or more than two of nitrate, formate, acetate, halide, carbonyl compound and organic acid with 1 to 5 carbon atoms. The precipitant is selected from one or more than two of ammonium carbonate, ammonium bicarbonate, lithium carbonate, lithium bicarbonate, sodium carbonate, sodium bicarbonate, potassium carbonate, potassium bicarbonate, magnesium carbonate and oxalic acid, preferably from ammonium carbonate, ammonium bicarbonate and potassium bicarbonate, and optimally from ammonium carbonate, ammonium bicarbonate and sodium bicarbonate. The precipitation temperature is controlled within a range of 2-80° C. The drying temperature is 80-150° C. and the time is longer than 12 h. The calcination temperature is 300-650° C. and time is 1-3 h. A calcination atmosphere could be flowing air or standing air.

The ultrasonic ion-exchange method includes dissolving two or more than three of metal precursors required by the multicomponent metal composite in a solvent to obtain two or more than three of metal cation solutions and then adding the inorganic solid acid with hierarchical pore structure into the solutions under ultrasonic agitation conditions. The ultrasonic method could be bath ultrasonic or tip ultrasonic method. The ultrasonic power is 1-20 W/(ml sample), and the frequency is 40 KHz-80 MHz. Precipitation temperature is 2-60° C., time is 1 h-12 h and the stirring rate is 50-500 rpm. Then, washing, drying and calcination are performed. The washing method may be filtration washing or centrifugal washing. The pH should be 6.5-7.5 after washing. Drying temperature is 80-150° C. and time is longer than 12 h. Calcination temperature is 300-650° C. and time is 1-3 h.

In the ball-milling method of the physical compounding method, the temperature is 25-100° C. The carrier gas is: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; or d) mixed gas of oxygen, nitrogen and/or inert gas, with the volume ratio of oxygen in the mixed gas being 5-20%. The inert gas is one or more than two of helium, argon and neon.

The mechanical mixing method in the physical compounding method achieves the purposes of separation, crushing, mixing and the like through one or more than two of extrusion force, impact force, shear force and friction force generated by high-speed motion of the material and the container by adding the multicomponent metal composite and the inorganic solid acid with hierarchical pore structures into the container by using a 3D rotary mixing instrument, a planetary mixer or a turbine mixing instrument, etc., so as to realize conversion of mechanical energy, thermal energy and chemical energy by regulating the temperature and the atmosphere of carrier gas, thereby further enhancing the interaction between different components. In the reaction process, the temperature is set as 20-100° C. The atmosphere of the carrier gas is: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; or d) mixed gas of oxygen, nitrogen and/or inert gas, with the volume ratio of oxygen in the mixed gas being 5-20%. The inert gas is one or more than two of helium, argon and neon.

Any of the catalysts is used to conduct the catalytic reaction to prepare $C_2$-$C_4$ light olefins, i.e., olefins containing two carbon atoms to four carbon atoms, including one or more than one of ethylene, propylene and butylene, at the required reaction temperature and reaction pressure with the volume ratio of the raw gas $H_2$/CO of 0.5/1 to 4/1.

Before the catalytic reaction, a pretreatment process of catalyst is conducted. The atmosphere of pretreatment is a) mixture of hydrogen and carbon monoxide, with the volume ratio of $H_2$/CO being 0.5/1 to 4/1;

or b) mixture of hydrogen and inert gas, with the volume ratio of hydrogen in the mixed gas being 5-100% and the inert gas being one or more than two of nitrogen, helium, argon or neon;

or c) mixture of carbon monoxide and inert gas, with the volume ratio of carbon monoxide in the mixed gas being 5-100% and the inert gas being one or more than two of nitrogen, helium, argon or neon.

The pretreatment temperature of the catalyst is 250-600° C. The pretreatment pressure is 0.1-3.0 MPa. The space velocity of pretreatment is 500-5000 $h^{-1}$, and preferably 1000-4000 $h^{-1}$.

Oxygen vacancies are generated in the surface structure after reduction activation of the metal composites with the atmosphere containing hydrogen or carbon monoxide. Namely, the metal is in a coordination unsaturated state and can efficiently catalyze and activate CO to generate one or more than two of intermediate species $CH_x$ (wherein x=1, 2 or 3). The surface oxygen species can react with CO to generate $CO_2$. The extremely active $CH_x$ species can be combined with CO to generate $CH_xCO$. The generated intermediate species are weakly absorbed on the surface, can easily desorb from the surface and diffuse into the pore channels of the inorganic solid acid and then be further catalyzed and converted into light olefins. The selectivity of the light olefins and a relative ratio of olefins to paraffins therein can be regulated by the pore channel size and the acidity of the inorganic solid acid.

The reaction raw gas is a mixed gas which contains $H_2$, CO and other gas. Other gas includes one or two of inert gas and/or non-inert gas.

The inert gas is one or more than two of nitrogen, helium, argon and neon. The volume ratio of inert gas in the reaction raw gas is less than 10%.

The non-inert gas is one or two of carbon dioxide, vaporized water, methanol and ethanol. The volume ratio of the non-inert gas in the reaction raw gas is less than 50%.

The volume ratio of $H_2$ to CO is 0.5/1 to 4/1.

The reactor adopted in the reaction is a fluidized bed, a moving bed or a fixed bed.

The temperature of the reaction is 300-500° C., and preferably 350-450° C. The space velocity is 500-10000 $h^{-1}$ and preferably 2000-7000 $h^{-1}$.

The reaction is operated in a continuous flow reaction mode or a batch reaction mode.

In the continuous flow reaction mode, the reaction pressure is 0.1-6.0 MPa, and preferably 1.0-5.0 MPa.

In the batch reaction mode, the reaction pressure is 1.0-10.0 MPa, and preferably 1.0-5.0 MPa.

TABLE 1

List of Cations and Anions of the Inorganic Acid Salts.

| Anion | Li | Na | Mg | Al | K | Ca | Sr | Ba | Ti | Cr | Mn | Fe | Co | Ni | Cu | Zn | Ga | Ge | Zr | Mo | Ru | Rh | Pd | Ag |
|---|---|---|---|---|---|---|---|---|---|---|---|---|---|---|---|---|---|---|---|---|---|---|---|---|
| $(Al_2O_4)^{2-}$ | ✓ | ✓ | ✓ |   | ✓ | ✓ | ✓ | ✓ |   |   | ✓ | ✓ | ✓ | ✓ | ✓ | ✓ | ✓ | ✓ |   | ✓ | ✓ | ✓ | ✓ | ✓ |
| $(SiO_3)^{2-}$ | ✓ | ✓ | ✓ | ✓ | ✓ | ✓ | ✓ | ✓ |   |   | ✓ | ✓ | ✓ | ✓ | ✓ | ✓ | ✓ | ✓ | ✓ | ✓ | ✓ | ✓ | ✓ | ✓ |
| $(SiO_4)^{4-}$ | ✓ | ✓ | ✓ | ✓ | ✓ | ✓ | ✓ | ✓ |   |   | ✓ | ✓ | ✓ | ✓ | ✓ | ✓ | ✓ | ✓ | ✓ | ✓ | ✓ | ✓ | ✓ | ✓ |
| $(TiO_3)^{2-}$ | ✓ | ✓ | ✓ | ✓ | ✓ | ✓ | ✓ | ✓ | ✓ |   | ✓ | ✓ | ✓ | ✓ | ✓ | ✓ | ✓ | ✓ | ✓ | ✓ | ✓ | ✓ | ✓ | ✓ |
| $(TiO_3)^{3-}$ | ✓ | ✓ | ✓ | ✓ | ✓ | ✓ | ✓ | ✓ | ✓ |   | ✓ | ✓ | ✓ | ✓ | ✓ | ✓ | ✓ | ✓ | ✓ | ✓ | ✓ | ✓ | ✓ | ✓ |
| $(VO_3)^{-}$ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ |
| $(VO_3)^{2-}$ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ |
| $(CrO_4)^{2-}$ | ✓ | ✓ | ✓ | ✓ | ✓ | ✓ | ✓ | ✓ | ✓ |   | ✓ | ✓ | ✓ | ✓ | ✓ | ✓ | ✓ | ✓ | ✓ | ✓ | ✓ | ✓ | ✓ | ✓ |
| $(Cr_2O_4)^{2-}$ | ✓ | ✓ | ✓ | ✓ | ✓ | ✓ | ✓ | ✓ |   |   | ✓ | ✓ | ✓ | ✓ | ✓ | ✓ | ✓ | ✓ | ✓ | ✓ | ✓ | ✓ | ✓ | ✓ |
| $(Mn_2O_4)^{2-}$ | ✓ | ✓ | ✓ | ✓ | ✓ | ✓ | ✓ | ✓ |   |   |   | ✓ | ✓ | ✓ | ✓ | ✓ | ✓ | ✓ | ✓ | ✓ | ✓ | ✓ | ✓ | ✓ |
| $(Fe_2O_4)^{2-}$ | ✓ | ✓ | ✓ |   | ✓ | ✓ | ✓ | ✓ |   |   |   | ✓ | ✓ | ✓ | ✓ |   |   |   | ✓ | ✓ | ✓ | ✓ | ✓ | ✓ |
| $(Co_2O_4)^{2-}$ | ✓ | ✓ | ✓ |   | ✓ | ✓ | ✓ | ✓ |   |   |   |   | ✓ | ✓ | ✓ |   |   |   | ✓ | ✓ | ✓ | ✓ | ✓ | ✓ |
| $(ZnO_2)^{2-}$ | ✓ | ✓ | ✓ |   | ✓ | ✓ | ✓ | ✓ |   |   |   |   |   |   |   |   |   |   |   | ✓ | ✓ | ✓ | ✓ | ✓ |
| $(Ga_2O_4)^{2-}$ | ✓ | ✓ | ✓ |   | ✓ | ✓ | ✓ | ✓ |   |   |   | ✓ | ✓ | ✓ | ✓ | ✓ |   |   |   | ✓ | ✓ | ✓ | ✓ | ✓ |
| $(GeO_3)^{2-}$ | ✓ | ✓ | ✓ |   | ✓ | ✓ | ✓ | ✓ |   |   |   | ✓ | ✓ | ✓ | ✓ | ✓ | ✓ |   |   | ✓ | ✓ | ✓ | ✓ | ✓ |
| $(GeO_4)^{4-}$ | ✓ | ✓ | ✓ |   | ✓ | ✓ | ✓ | ✓ |   |   |   | ✓ | ✓ | ✓ | ✓ | ✓ | ✓ |   |   | ✓ | ✓ | ✓ | ✓ | ✓ |
| $(MoO_4)^{2-}$ | ✓ | ✓ | ✓ |   | ✓ | ✓ | ✓ | ✓ |   |   |   | ✓ | ✓ | ✓ | ✓ | ✓ |   |   |   | ✓ | ✓ | ✓ | ✓ | ✓ |
| $(CeO_3)^{2-}$ | ✓ | ✓ | ✓ | ✓ | ✓ | ✓ | ✓ | ✓ | ✓ |   | ✓ | ✓ | ✓ | ✓ | ✓ | ✓ |   |   |   | ✓ | ✓ | ✓ | ✓ | ✓ |
| $(ZrO_3)^{2-}$ | ✓ | ✓ | ✓ | ✓ | ✓ | ✓ | ✓ | ✓ |   |   | ✓ | ✓ | ✓ | ✓ | ✓ | ✓ | ✓ | ✓ |   | ✓ | ✓ | ✓ | ✓ | ✓ |
| $(SrO_3)^{4-}$ | ✓ | ✓ | ✓ | ✓ | ✓ | ✓ | ✓ | ✓ |   |   | ✓ | ✓ | ✓ | ✓ | ✓ | ✓ | ✓ | ✓ | ✓ | ✓ | ✓ | ✓ | ✓ | ✓ |

The present invention relates to a method for directly converting synthesis gas into light olefins by a one-step process. Light olefins products comprise two or more than two of ethylene, propylene and butylene. The content of the light olefins products in all hydrocarbons is 50%-85%.

The present invention has the following advantages:

Compared with traditional Fischer-Tropsch reaction route that produces light olefins also by a one-step process, the present invention has the following features:

1. The product distribution does not obey the Anderson-Schultz-Flory distribution rule controlled by surface polymerization mechanism. In the traditional Fischer-Tropsch reaction, the predicted selectivity of $C_2$-$C_4$ hydrocarbons is no more than 58%, while the selectivity of $C_2$-$C_4$ hydrocarbons provided by the present invention reaches 60%-95%.

2. The selectivity of the light olefins in the total hydrocarbon product is up to 50%-85%.

3. The selectivities of methane and $C_{5+}$ long-carbon-chain hydrocarbon in the products are very low. The total selectivity of both two cut fractions is 5%-10%.

4. The catalyst is different from those used in the traditional light olefins synthesis process via Fischer-Tropsch reaction, which contains principal components of transition metal such as Fe, Co and the like. The catalyst is a composite catalysis material containing the inorganic solid acid with a hierarchical pore structure and the multicomponent metal composite.

Compared with the already industrialized two-stage method that is a process of first converting synthesis gas into methanol or dimethyl ether, followed by converting the methanol or dimethyl ether into light olefins, the present invention has the following features:

1. One reactor, one catalyst and one-step conversion from synthesis gas can significantly reduce the capital investment and production cost.

2. The catalyst is the catalytic material formed by compounding the inorganic solid acid with a hierarchical pore structure and the multicomponent metal composite. The selectivity of the products can be well regulated.

3. The catalyst has a good stability and a long life.

4. The present invention has the advantages of single operation unit, good process reproducibility, high product selectivity, long catalyst life (>500 h) and wide industrial application potentials.

The catalysts provided in the present invention have the following advantages: in synthesis of light olefins from synthesis gas, the catalyst provided by the present invention is a composite material obtained by compounding the multicomponent metal composite and the inorganic solid acid with a hierarchical pore structure. The catalyst is different from those used in the traditional light olefins synthesis process via Fischer-Tropsch reaction, which contains principal components of transition metal such as Fe, Co and the like; and is also different from the catalysts used in methanol synthesis by the industrial two-stage method. The innovations include the structures and functions: in the aspect of the structure, the catalyst has the hierarchical pore structure of micropores and mesopores at the same time. The unique structure allows the catalyst to have a distinct advantage, that is a long life time (>500 h) without deactivation under the reaction conditions. In the aspect of the function, the present invention can directly catalyze the conversion of the synthesis gas, without the need of the high-energy-consuming water-gas shift process or the process of converting the synthesis gas into methanol and extracting the methanol. The one-step process is also different from the traditional chain growth mechanism of Fischer-Tropsch synthesis route. The light hydrocarbon products can be generated by the one-step process. The selectivity of the light hydrocarbons is 60%-95%. This is obviously beyond the selectivity limit predicted by the Anderson-Schultz-Flory distribution model following the traditional Fischer-Tropsch reaction. In addition, and the selectivity of methane and the long-chain hydrocarbon product ($C_{5+}$) is less than 5%-10%.

DETAILED DESCRIPTION

Figure 1:
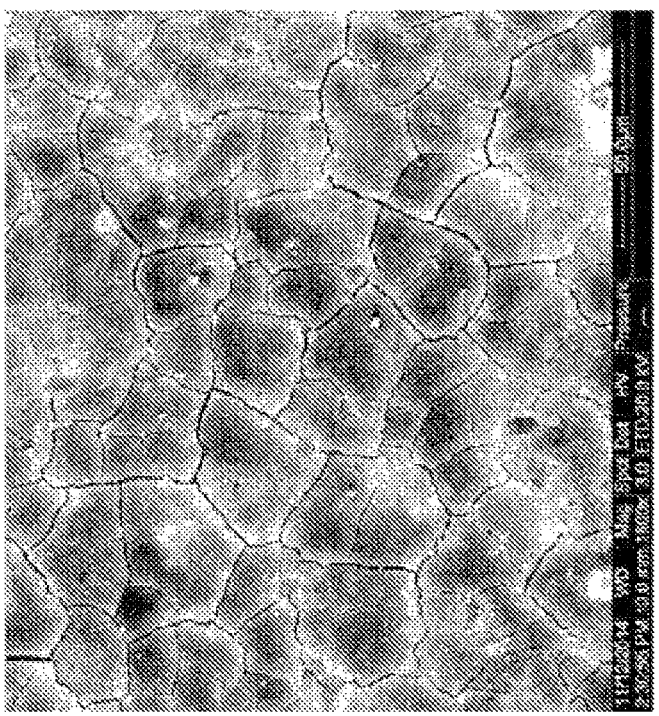
FIG. 1 is an SEM picture of $Cu_1Zn_1$@SiAl of a core-shell structure in embodiment 8.
Figure 1:
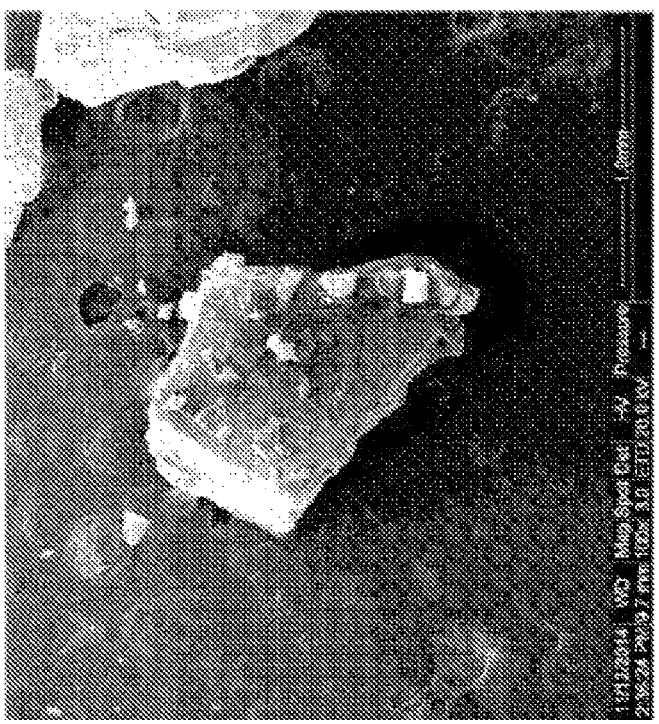
Figure 2:
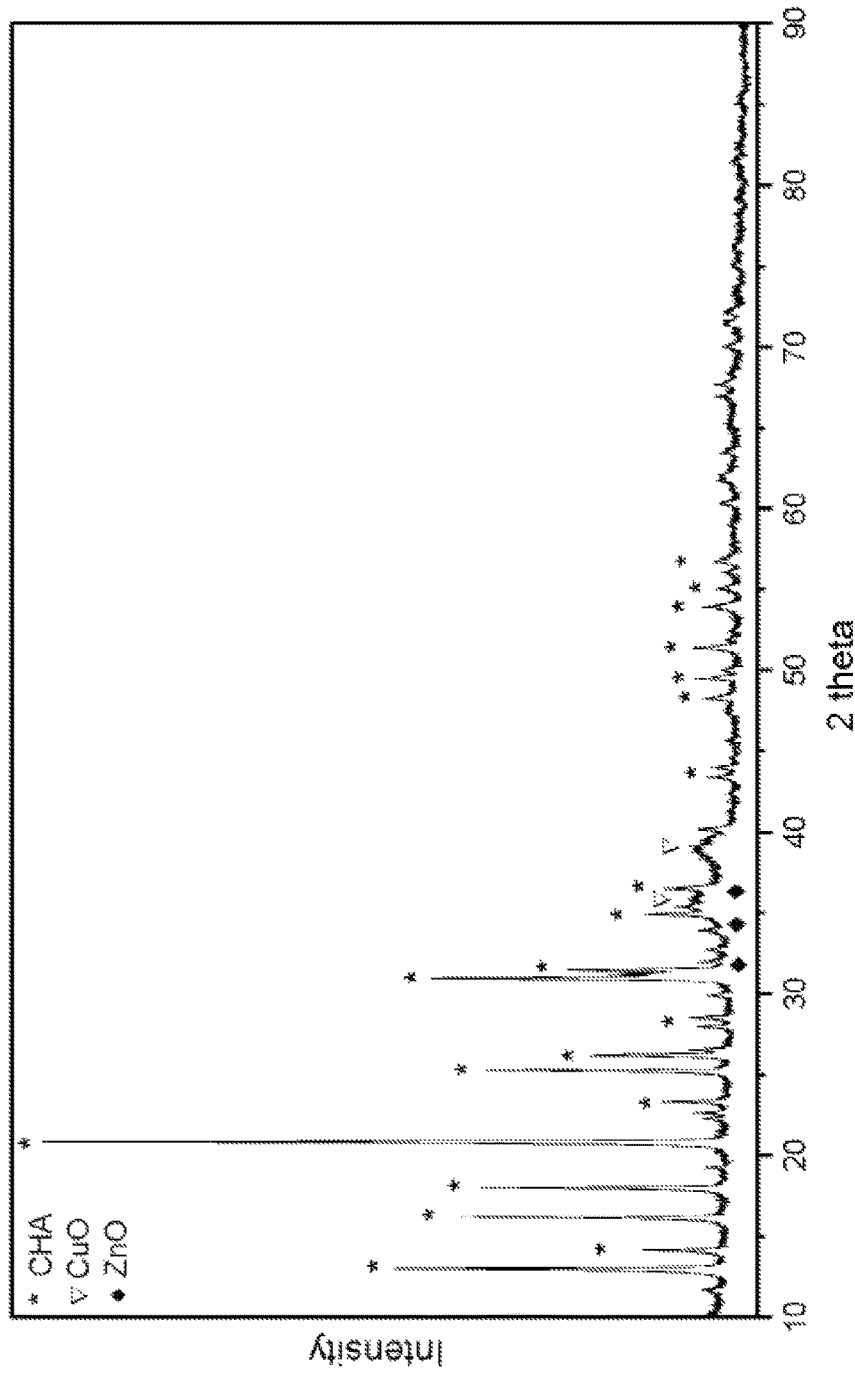
FIG. 2 is an XRD graph of $Cu_1Zn_1$@SiAl in embodiment 8.
Figure 3:
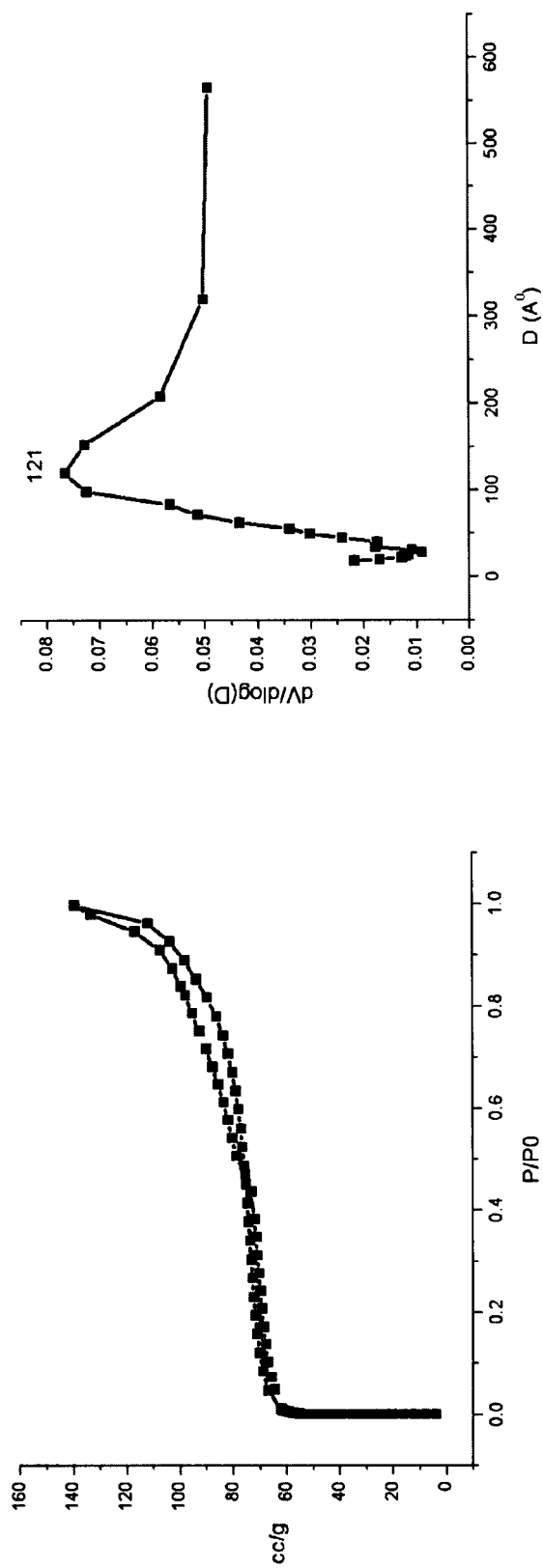
FIG. 3 is an $N_2$ physical adsorption curve and a pore diameter distribution diagram of silicon-phosphorus-aluminum inorganic solid acid with a hierarchical pore structure in embodiment 14.
Figure 4:
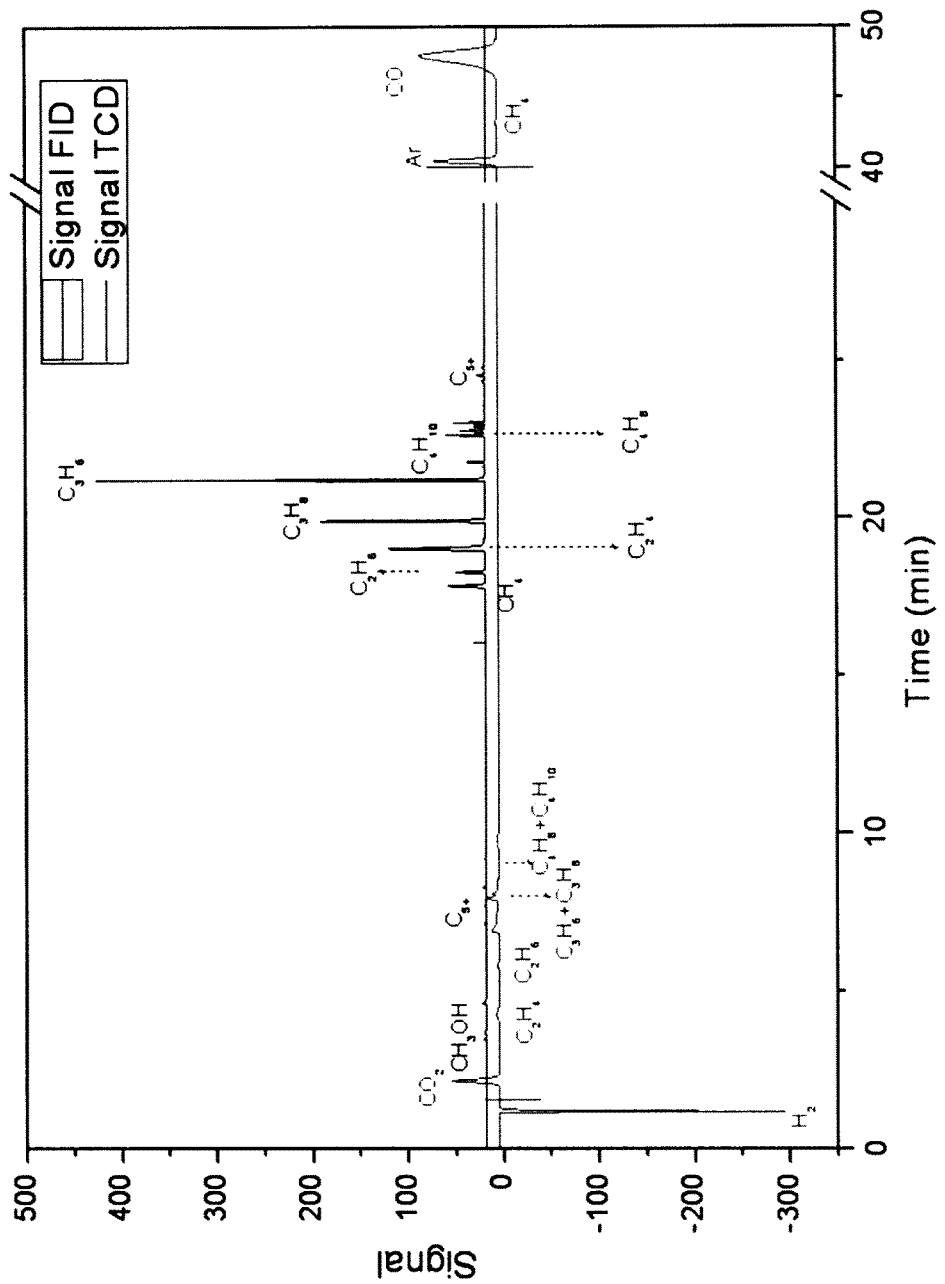
FIG. 4 is a chromatogram of the on-line chromatographic analysis of direct conversion of synthesis gas into products in embodiment 6.

The present invention is further illustrated below by the embodiments, but the scope of claims of the present invention is not limited by the embodiments. Meanwhile, the embodiments only give some conditions for achieving the purpose, but it doesn't mean that the conditions must be satisfied to achieve the purpose.

Example of Catalytic Reactions

A continuous flow fixed bed reaction is taken as an example, but the catalyst is also applicable to a fluidized bed reactor. The apparatus is equipped with gas mass flow meters, gas deoxidization and dehydration tubes, and online product analysis chromatography (the tail gas of the reactor is directly connected with the metering valve of chromatography, and thus periodic and real-time sampling and analysis will be achieved). Before use, the above catalyst is compressed and sieved into particles of 20-40 meshes or 40-60 meshes for later use.

2.8 g of catalyst in the following embodiments or reference examples is placed in a fixed bed reactor. The air in the reactor is replaced with Ar; and then reduction is conducted in a pure $H_2$ atmosphere at 310° C.-350° C. for 1 h. The temperature is cooled to room temperature in the Ar atmosphere, and then the Ar atmosphere is switched to synthesis gas (5% Ar; $H_2$/CO=2/1). The temperature is raised to reaction temperature, and the air velocity and the pressure of the reaction raw gas are regulated. The on-line chromatography is used to detect and analyze the product. The reaction performance can be changed by changing the temperature, pressure, space velocity and $H_2$/CO ratio.

Embodiment 1

A composite catalyst of the multicomponent metal composite and the inorganic solid acid with a hierarchical pore structure is prepared by a chemical compounding method.

The multicomponent metal composite of CuZnAl and silicon-aluminum inorganic solid acid with a hierarchical pore structure are taken as examples.

The raw materials of 30% silica sol (mass concentration), aluminum sulfate, sodium hydroxide, N,N,N-trimethyl-adamantane ammonium hydroxide (R) and deionized water are weighed according to the oxide $SiO:Al_2O_3:Na_2O:R_2O:H_2O$=40:1:16:5:900 (mass ratio); after mixing at room temperature and stirring at 60° C. and 200 rpm for 24 h, the mixture is transferred to a hydrothermal reactor and crystallized at 155° C. for 6 d. The mixture is naturally cooled to room temperature and transferred to a beaker to have a water bath at 70° C. Ammonium chloride is added according to a ratio of 100 ml of stock solution to 4 g of ammonium chloride, stirred at constant temperature for 3 h and subjected to centrifugal washing repeatedly so that the pH of the supernatant is 7 at the end of washing. After the precipitate is dried at 120° C. for 24 h, the precipitate is calcined in air at 650° C. for 3 h to obtain the silicon-aluminum inorganic solid acid with hierarchical pore structure.

5.3 g of the prepared silicon-aluminum inorganic solid acid with hierarchical pore structure is weighed; 1.2 g of copper nitrate trihydrate, 1.49 g of zinc nitrate hexahydrate and 1.8 g of aluminum nitrate nonahydrate are taken and dissolved into 100 ml of aqueous solution; CuZnAl is introduced into the silicon-aluminum inorganic solid acid with hierarchical pore structure through an immersion method, dried in vacuum at room temperature and calcined in still air at 500° C. for 1 h to obtain $Cu_1Zn_1Al_1$/mesoSiAl with a mole ratio of elements of 1:1:1. The loading capacity of the multicomponent metal composite is 20 wt %. According to the method, the metal components and the proportions thereof as well as the loading capacity of the multicomponent metal composite can be changed.

The $N_2$ physical adsorption and desorption show that the catalyst has a hierarchical pore structure. The microporous specific surface area is 347 $m^2/g$ with micropore size distribution of 3-4 Å, and the mesoporous specific surface area is 214 $m^2/g$ with mesopore size distribution of 2-15 nm, and the macroporous specific surface area is 62 $m^2/g$.

X-ray diffraction (XRD) shows that the multicomponent metal composite contains CuO, ZnO, $Al_2O_3$, $ZnAlO_2$ and the silicon-aluminum inorganic solid acid with CHA topology, the crystal size of the metal oxide is 5-15 nm and the crystal size of the inorganic solid acid is 40-70 nm. Scanning electron microscopy (SEM) shows that the secondary particle size of the silicon-aluminum inorganic solid acid with hierarchical pore structure is 10-100 μm and the crystal size of the inorganic solid acid is 10-100 nm. High resolution transmission electron microscopy (HRTEM) shows that the crystal size of the multicomponent metal composite is 5-15 nm and the secondary particle size is 15-50 nm. $NH_3$ desorption peak temperature corresponding to medium strong acid is 360° C., and the amount of sites of the medium strong acid is 2 mol/kg. The medium strong acid is defined according to $NH_3$-TPD and is the position of a desorption peak according to $NH_3$. The position of the desorption peak means that under standard test conditions that a ratio of sample mass w and carrier gas flow rate f is 100 g·h/L and a heating rate is 10° C./min, a TCD records a thermal conductivity signal of desorption of NH3 and draws a desorption curve; according to peaks in positions of curve peaks, the inorganic solid is divided into three acid intensities. The medium strong acid is an acid site where the deposition temperature of $NH_3$ is between 275° C. and 500° C.

Embodiment 2

The preparation process is substantially the same as that of embodiment 1, and the difference is that in the preparation process of the silicon-aluminum inorganic solid acid with a hierarchical pore structure in embodiment 1, the crystallization temperature is changed to 150° C. for 5 days to prepare the silicon-aluminum inorganic solid acid of CHA topology with the amount of sites of the medium strong acid of 0.8 mol/kg.

In the reference example 1, the preparation process is substantially the same as that of embodiment 1, and the difference is that in the preparation process of the silicon-aluminum inorganic solid acid with hierarchical pore structure in embodiment 1, the crystallization temperature is changed to 140° C. for 3 days to prepare the silicon-aluminum inorganic solid acid with the amount of sites of the medium strong acid of 0.01 mol/kg.

In the reference example 2, the preparation process is substantially the same as that of embodiment 1, and the difference is that in the preparation process of the silicon-aluminum inorganic solid acid with hierarchical pore structure in embodiment 1, the crystallization temperature is changed to 140° C. for 22 h to prepare the silicon-aluminum inorganic solid acid with the amount of sites of the medium strong acid of 0.005 mol/kg.

Under reaction conditions of 365° C., 2 MPa and volume space velocity of 4000 $h^{-1}$, reaction results are shown in the table below.

| Catalyst | CO Conversion % | $CH_x$ Selectivity % | $CH_4$ Selectivity % | $C_2$-$C_4$ Hydrocarbon Selectivity % | $C_2^=$-$C_4^=$ Olefin Selectivity % | $C_{5+}$ Selectivity % |
|---|---|---|---|---|---|---|
| Embodiment 1 | 15.63 | 54.56 | 1.71 | 88.77 | 50.56 | 9.52 |
| Embodiment 2 | 6.14 | 55.80 | 5.96 | 79.41 | 50.27 | 14.63 |
| Reference Example 1 | 2.33 | 70.39 | 37.63 | 34.17 | 13.79 | 28.20 |
| Reference Example 2 | 1.28 | 68.17 | 41.29 | 45.62 | 11.08 | 13.09 |

The CO conversion in the reference examples 1 and 2 are very low because of the low amount of the sites of the medium strong acid in the solid acid, resulting in that the intermediate species generated on the multicomponent metal composite cannot be timely and well converted into the target product. Meanwhile, methane selectivity is increased greatly to be more than 30%, while the selectivity of the light olefins is also reduced significantly. In contrast, the CO conversion of the catalyst containing more medium strong acid in the present invention is greatly increased, and the selectivity of the target product olefins is also high. The CO conversion in embodiment 1 is significantly higher than that in embodiment 2 because the catalyst is within the preferred range. It can be seen that the acid content of the silicon-aluminum inorganic solid acid with hierarchical pore structure is extremely important for the control of the catalytic properties including the CO conversion and the selectivity.

Embodiment 3

A composite catalyst of the multicomponent metal composite and the silicon-phosphorus-aluminum inorganic solid acid with hierarchical pore structure is prepared by a chemical compounding method.

The raw materials of 30% silica sol (mass concentration), aluminum sulfate, phosphoric acid, TEA (R) and deionized water are weighed according to the oxide $SiO:Al_2O_3$:

$H_3PO_4:R:H_2O=18:16:32:55:150$ (mass ratio); after mixing at room temperature, stirring and aging at 30° C. and stirring at 500 rpm for 72 h, the mixture is transferred to a hydrothermal reactor and crystallized at 220° C. for 15 h. The water bath is quenched to room temperature. Centrifugal washing is conducted repeatedly so that the pH of the supernatant is 7 at the end of washing. After the precipitate is dried at 130° C. for 17 h, the precipitate is calcined in air at 580° C. for 5 h to obtain the silicon-phosphorus-aluminum inorganic solid acid with hierarchical pore structure.

2.1 g of the silicon-phosphorus-aluminum inorganic solid acid with hierarchical pore structure is weighed; 1.54 g of zinc nitrate hexahydrate and 3.8 g of aluminum nitrate nonahydrate are taken and dissolved into an aqueous solution to prepare a mixed solution A; 6.3 g of ammonium carbonate is weighed and dissolved in 100 ml of water to prepare a solution B; the solution B is dropwise added at 50° C. to the mixed solution A stirred at a power of 7 W with tip ultransonic and a speed of 400 rpm; centrifugal washing is conducted so that the pH of the supernatant is 7 at the end of washing; the mixture is dried in the air at 110° C. and calcined in still air at 500° C. for 2 h to obtain $ZnCr_{1.8}/SiPAl$. Then, through $ZnCr_{1.8}/SiPAl$ as a carrier, 0.057 g of palladium diacetate $Pd(Ac)_2$ is accurately weighed and dissolved in acetone, and introduced into $ZnCr_{1.8}/SiPAl$ by impregnation, wherein the mole ratio of Pd to Zn is 0.01. $Pd_{0.01}ZnCr_{1.8}/SiPAl$ with the element mole ratio of 0.01:1:1.8 is obtained. The loading capacity of the multicomponent metal composite is 20 wt %. According to the method, the metal components and the proportions thereof as well as the loading capacity of the multicomponent metal composite can be changed.

The $N_2$ physical adsorption and desorption show that the catalyst has a hierarchical pore structure. Micropore size distribution is in the range of 4-5 Å, while mesopore size distribution in 2-8 nm. The total specific surface area is 416 $m^2/g$, with 35% of the mesoporous specific surface area and 20% of the macroporous specific surface area. X-ray diffraction (XRD) shows that the multicomponent metal composite contains $Cr_2O_3$, $CrO_3$, ZnO, $Al_2O_3$, $ZnCr_2O_4$ and the silicon-aluminum inorganic solid acid with CHA topology, and the crystal size of the metal oxide and the crystal size of the inorganic solid acid are 7-16 nm and 50-60 nm, respectively. Scanning electron microscopy (SEM) shows that the secondary particle size of the silicon-aluminum inorganic solid acid is 100-500 μm. High resolution transmission electron microscopy (HRTEM) shows that the crystal size of the multicomponent metal composite is 7-16 nm and the secondary particle size is 20-100 nm. $NH_3$ desorption peak temperature corresponding to medium strong acid is 386° C., and the amount of sites of the medium strong acid is 6 mol/kg.

Embodiment 4

The preparation process is substantially the same as that of embodiment 3, and the difference is that in preparation of the silicon-aluminum inorganic solid acid, the stirring time is changed to 3 h, and the crystallization time is changed to 24 h to prepare the silicon-aluminum inorganic solid acid of CHA topology, with the total specific surface area of 377 $m^2/g$, including 21% of mesoporous specific surface area and 20% of macroporous specific surface area. $NH_3$ desorption peak temperature corresponding to medium strong acid is 385° C., and the amount of sites of the medium strong acid is 5.8 mol/kg.

In the reference example 3, the preparation process is substantially the same as that of embodiment 3, and the difference is that in preparation of the silicon-aluminum inorganic solid acid, the aging temperature is changed to 80° C., and the crystallization is conducted at 240° C. for 24 h after stirring for 2 d to obtain the silicon-aluminum inorganic solid acid of CHA topology, with the total specific surface area of 232 $m^2/g$, including 4% of mesoporous specific surface area and 1% of macroporous specific surface area. $NH_3$ desorption peak temperature corresponding to medium strong acid is 411° C., and the amount of sites of the medium strong acid is 2 mol/kg.

In the reference example 4, the preparation process is substantially the same as that of embodiment 3, and the difference is that in preparation of the silicon-aluminum inorganic solid acid, the aging temperature is changed to 30° C., and the crystallization is conducted at 240° C. for 48 h after stirring for 2 d to obtain the silicon-aluminum inorganic solid acid of CHA topology, with the total specific surface area of 287 $m^2/g$, including 10% of mesoporous specific surface area and 4% of macroporous specific surface area. $NH_3$ desorption peak temperature corresponding to medium strong acid is 390° C., and the amount of sites of the medium strong acid is 5 mol/kg.

In the reference example 5, the preparation process is substantially the same as that of embodiment 3, and the difference is that in preparation of the silicon-aluminum inorganic solid acid, through calculation by the specific surface area, a commercial SBA-15 molecular sieve with mesopore size distribution of 4-8 nm is mechanically mixed with the silicon-aluminum inorganic solid acid in the reference example 3; the mixing ratio is 13:7 in terms of the specific surface area of the silicon-aluminum inorganic solid acid to SBA-15; and then the mixture is ground and mixed to obtain the silicon-aluminum inorganic solid acid having mesoporous and microporous composite, wherein the proportions of microporous, mesoporous and macroporous specific surface areas in total specific surface area are 62%, 36% and 2% respectively. But the mesopore channels with diameters of 2-50 nm are not formed by stacking inorganic solid acid crystal particles, wherein the primary pores are not located in pore walls of adjacent secondary pores and/or tertiary pores, but the primary pores exist alone, while the secondary and tertiary pore channels also exist alone. The three kinds of pore channels not in conformity with the claims are mutually connected and do not constitute a three-dimensional hierarchical pore channel structure.

Under reaction conditions of 400° C., 2.5 MPa and volume space velocity of 4000 $h^{-1}$, reaction results are shown in the table below.

| Catalyst | CO Conversion % | $CH_x$ Selectivity % | $CH_4$ Selectivity % | $C_2$-$C_4$ Hydrocarbon Selectivity % | $C_2^=$-$C_4^=$ Olefins Selectivity | $C_{5+}$ Selectivity % |
|---|---|---|---|---|---|---|
| Embodiment 3 | 22.78 | 59.35 | 1.64 | 95.66 | 80.04 | 2.7 |
| Embodiment 4 | 20.11 | 58.09 | 4.90 | 85.16 | 60.57 | 9.94 |
| Reference Example | 13.83 | 57.90 | 10.84 | 77.93 | 5.77 | 11.23 |

| Catalyst | CO Conversion % | CH$_x$ Selectivity % | CH$_4$ Selectivity % | C$_2$-C$_4$ Hydrocarbon Selectivity % | C$_2^=$-C$_4^=$ Olefins Selectivity | C$_{5+}$ Selectivity % |
|---|---|---|---|---|---|---|
| Reference Example | 17.36 | 59.26 | 6.28 | 86.99 | 25.74 | 6.73 |
| Reference Example | 13.55 | 54.28 | 11.73 | 79.64 | 8.02 | 8.63 |

The selectivity of the light olefins in embodiment 3 is significantly better than that in reference examples 3 and 4, and even better than that in embodiment 4 because in embodiment 3, the proportions of the mesoporous specific surface area to and the macroporous specific surface area to total specific surface area of the silicon-aluminum inorganic solid acid are 35% is 20% and are within a more preferred range compared with the proportions of the mesoporous specific surface area and the macroporous specific surface area to total specific surface area: 21% and 20% in embodiment 4. Therefore, the mass transfer is better, thereby inhibiting the production of alkanes from hydrogenation, and increasing the selectivity greatly. However, the selectivity of the light olefins in the reference example is far below the selectivity of the catalyst of the present invention because the number of mesopores and macropores of the molecular sieve is too small and fail to reach the content of the mesopores and the macropores in claims. Therefore, mass transfer is not convenient. Meanwhile, the change of acid intensity causes excessive hydrogenation in the product to produce alkane, thereby greatly reducing the selectivity of the light olefins. In the reference example 5, although the content of the mesopores and the macropores conform to the ranges in claims, three kinds of contained pore channels are not mutually connected and communicated, and do not form the three-dimensional three-level pore channel structure in claims. In addition, the medium strong acid on the surface and in the pore channels of SBA-15 is little. Therefore, the medium strong acid in the reference example 5 is mainly distributed in the micropores, instead of being uniformly distributed in the three-dimensional three-level pore channels inconsistent with claim 5. Thus, no substantial change is made compared with the reference example 3, and the selectivity of the light olefins is still very low. In contrast, for catalyst with the three-dimensional hierarchical pore channel structure having 20-75% of mesoporous specific surface area and 20-65% of macroporous specific surface area, the selectivity of olefins is greater than 60%, which is not only much higher than that of the reference examples 3 and 4, but also higher than the theoretical selectivity 58% of light olefins of traditional Fischer-Tropsch synthesis. It can be seen that the pore channel structure of the inorganic acid is extremely important for the control of the product selectivity.

Embodiment 5

Preparation of a composite catalyst of multicomponent metal composite and silicon-phosphorus-aluminum inorganic solid acid with hierarchical pore structure through a physical compounding method. The method comprises mixing different materials by means of ball milling, mechanical mixing instrument, shaker, oscillation shocker mixing and the like.

The silicon-phosphorus-aluminum inorganic solid acid with hierarchical pore structure: the crosslinking agent of triethylamine, gelatin and glutaraldehyde is used as a template. 10 g of aluminum isopropoxide, 5.30 g of strong phosphoric acid, 3.67 g of silica sol (a mass concentration of 30%), 1.46 g of triethylamine and 13.2 g of H$_2$O are mixed and stirred at room temperature for 3 h at a stirring speed of 400 rpm. Then 1.68 g of 2 wt % gelatin solution is added, heated to 57° C. and continuously stirred for 0.5 h. The obtained mixed solution is poured into a culture dish and frozen at 0° C. for 12 h to obtain gel. An appropriate amount of 5 wt % glutaraldehyde is added to have a crosslinking reaction. The suspension after the reaction is centrifuged at 10000 rpm. The obtained solid sample is dried in a 50° C. oven overnight and then filled in a Teflon liner. The small Teflon liner is placed in a larger Teflon liner to which an appropriate amount of the mixed solution of triethylamine and water is added in advance. Then, the larger and the smaller liners are filled together into a stainless steel self-pressure crystallization kettle, crystallized at 200° C. through a dry gum method for 36 h, and subjected to repeated centrifugal washing so that pH of the supernatant is 7 at the end of washing. The precipitate is dried at 90° C. for 6 h, and calcined in air at 550° C. for 3 h after drying at 110° C. for 12 h to obtain the silicon-phosphorus-aluminum inorganic solid acid with hierarchical pore structure.

17.33 g of zinc nitrate hexahydrate and corresponding amount of copper nitrate hexahydrate, cobalt nitrate hexahydrate and chromium nitrate nonahydrate are respectively weighed according to a molar ratio of the metal elements Zn:Cu:Co:Cr:Al of 6:0.2:1:1:1 and dissolved in 100 ml of deionized water. Y—Al$_2$O$_3$ is added and subjected to ultrasonic agitation at 25° C., with the tip ultrasonic power of 5 W and stirring speed of 300 rpm. Then, the mixture is dried in air at 110° C. and calcined at 500° C. to obtain the multicomponent metal composite Zn$_6$Cu$_{0.2}$Co$_1$Cr$_1$Al$_1$ with element molar ratio of 6:0.2:1:1:1.2 g of the multicomponent metal composite and 5 g of the silicon-phosphorus-aluminum inorganic solid acid with hierarchical pore structure are placed in Teflon mixing tank. The air is replaced three times by helium at first, and then 2% H$_2$ (He balance) is introduced into the tank. The mixing tank is then closed and mixed at a rate of 450 rpm for 5 minutes to prepare the composite catalysts Zn$_6$Cu$_{0.2}$Co$_1$CrAl/SiPAl, wherein the multicomponent metal composite accounts for 40 wt % of the total mass of the catalyst. In this way, the content of the multicomponent metal composite and the kind of the inorganic solid acid with hierarchical pore structure can be changed.

The N$_2$ physical adsorption and desorption show that the catalyst has a hierarchical pore structure. The microporous specific surface area is 243 m$^2$/g with micropore size distribution of 4-5 Å, the mesoporous specific surface area is 318 m$^2$/g with mesopore size distribution of 15-25 nm, and the macroporous specific surface area is 182 m$^2$/g. NH$_3$ desorption peak temperature corresponding to medium strong acid is 367° C., and the amount of sites of the medium strong acid is 1.5 mol/kg.

In embodiment 6, the preparation process is substantially the same as that of embodiment 5, and the difference is that content of the multicomponent metal composite is adjusted to 15 wt %, based on 100% of the total mass of the catalyst.

In reference example 6, the preparation process is substantially the same as that of embodiment 5, and the difference is that content of the multicomponent metal composite is adjusted to 5 wt %, based on 100% of the total mass of the catalyst.

In reference example 7, the preparation process is substantially the same as that of embodiment 5, and the difference is that content of the multicomponent metal composite is adjusted to 90 wt %, based on 100% of the total mass of the catalyst.

Embodiment 7

The preparation process is substantially the same as that of embodiment 5, and the difference is that in preparation of the silicon-phosphorus-aluminum inorganic solid acid with hierarchical pore structure, the crystallization temperature is changed to 190° C., the time is 33 h; and calcination temperature is 600° C. and the time is 3 h. The $N_2$ physical adsorption and desorption show that the catalyst has a hierarchical pore structure, with the micropore size distribution of 10-15 nm. Scanning electron microscopy (SEM) shows that the secondary particle size of the silicon-aluminum inorganic solid acid is 10-70 μm and the crystal size of the inorganic solid acid is 60-80 nm. $NH_3$ desorption peak temperature of medium strong acid is 385° C., and the amount of sites of the medium strong acid is 1.5 mol/kg.

In reference example 8, the preparation process is substantially the same as that of embodiment 7, and the difference is that in preparation of the silicon-phosphorus-aluminum inorganic solid acid with hierarchical pore structure, the crystallization temperature is changed to 160° C., the time is 24 h; and calcination temperature is 550° C. and the time is 8 h. Calcination is conducted under flowing air. The $N_2$ physical adsorption and desorption show that the catalyst has a hierarchical pore structure, with the mesopore size distribution of 2-5 nm. Scanning electron microscopy (SEM) shows that the secondary particle size of the silicon-aluminum inorganic solid acid is 5-100 nm and XRD shows that the crystal size of the inorganic solid acid is 1-5 nm. $NH_3$ desorption peak temperature corresponding to medium strong acid is 349° C., and the amount of sites of the medium strong acid is 0.06 mol/kg.

Under reaction conditions of 370° C., 2 MPa and volume space velocity of 6000 $h^{-1}$, reaction results are shown in the table below.

| Catalyst | CO Conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 5 | 6.67 | 54.88 | 3.04 | 82.91 | 62.11 | 14.05 |
| Embodiment 6 | 4.17 | 55.34 | 3.29 | 83.66 | 56.77 | 13.05 |
| Reference Example 6 | 3.30 | 62.17 | 70.71 | 20.56 | 10.38 | 8.73 |
| Reference Example 7 | 1.22 | 53.03 | 5.74 | 50.64 | 46.11 | 43.62 |
| Embodiment 7 | 13.78 | 62.72 | 2.97 | 86.03 | 66.84 | 11.00 |
| Reference Example 8 | 2.58 | 27.38 | 44.69 | 47.90 | 28.15 | 7.41 |

The CO conversion in reference examples 6 and 7 are far below the CO conversion in embodiments. The methane selectivity in reference example 6 is as high as 70%, while the selectivity of $C_{5+}$ in reference example 7 exceeds 40% and the selectivity of light olefins is also lower than the result of the catalyst in the present invention because the content of the proportional multicomponent metal composite in the entire catalyst does not conform to the content range described in claims and is not conducive to the conversion of intermediate species produced during the reaction. By comparing embodiment 5 with embodiment 6, selectivities of light olefins in the two embodiments exceed 50% and methane selectivities are less than 5%. However, the CO conversion in embodiment 5 is higher because the content of the multicomponent metal composite in the entire catalyst in embodiment 5 is in the preferred range, so the CO conversion is higher.

For the silicon-phosphorus-aluminum inorganic solid acid with hierarchical pore structure in embodiments 6 and 7, the crystal size, the size of secondary particles stacked by the crystal particles and mesopore channel size are within the range of the claims. However, relative to embodiment 6, the crystal size, the size of secondary particles and mesopore channel size in embodiment 7 are within the preferred range, so embodiment 7 shows better CO conversion and selectivity. However, reference example 8 is not within the claims, shows that the crystallization degree of inorganic solid acid is not good, and catalytic conversion cannot be better conducted. Therefore, the CO conversion and the selectivity are significantly worse. Thus, the crystal size, the secondary particle size and the mesopore channel size of the inorganic solid acid are extremely important for the control of the catalytic conversion and the product selectivity.

Embodiment 8

A composite catalyst of the multicomponent metal composite and the inorganic solid acid with hierarchical pore structure is prepared by a coating growth method.

The method relates to the growth of a single layer or a part of inorganic solid acid material with hierarchical pore structure on the prepared multicomponent metal composite by a hydrothermal method and the like.

By taking CuZn metal and co-precipitation method as an example, the method is not limited to bimetal and is suitable for other metals, and the relative proportion of different metals can be changed. Ammonia, ammonium carbonate or ammonium bicarbonate can be used as a precipitant.

4.8 g of copper nitrate trihydrate and 5.95 g of zinc nitrate hexahydrate are weighed and dissolved in 100 ml of deionized water. 11 g of ammonium carbonate is weighed and dissolved in 100 ml of deionized water. The two groups of solutions are simultaneously added dropwise to the deionized water under ultrasonic agitation at constant temperature of 70° C. and precipitated, with an ultrasonic power of 5 W and a stirring rate of 500 rpm. Then, the precipitate is aged at 70° C. for 3 h and washed with 70° C. of deionized water to be neutral. Then, the precipitate is dried at 110° C. for 12 h and calcined at 500° C. for 1 h to prepare CuZn composite oxide, wherein Cu/Zn mole ratio is 1:1. By this method, CuZn oxide of different molar ratios can be obtained.

10 ml of silica sol solution (containing 30 wt % of $SiO_2$) is added to 10 ml of deionized water; 1 g of the above multicomponent metal composite is weighed and added to the solution; the mixture is infiltrated by solution at shaking table for 2 h so that the solid and liquid are separated; the solid is placed in an oven of 120° C. and dried for 12 h and calcined at 500° C. for 2 h so that the oxide is covered with a layer of SiO$_2$ film; and 11.37 g of TPAOH, 9.68 g of ethanol, 0.06 g of aluminium oxide and 50 ml of H$_2$O are weighed, stirred and dissolved. The above oxide is added, and stirred. 9.65 g of TEOS is weighed and dropwise added to the above solution, and stirred for 6 h. The mixture is crystallized at 180° C. for 72 h, filtered and washed, dried in an oven of 60° C. and calcined at 500° C. for 5 h to obtain the Cu$_1$Zn$_1$@SiAl catalyst with a core-shell structure, wherein the oxide accounts for 50 wt % of the total mass of the catalyst. According to the method, the metal components and the proportions thereof as well as the loading capacity of the multicomponent metal composite can be changed.

The N$_2$ physical adsorption and desorption show that the catalyst has a hierarchical pore structure. The microporous specific surface area is 311 m$^2$/g with micropore size distribution of 3-4 Å, and the mesoporous specific surface area is 203 m$^2$/g with mesopore size distribution of 13-30 nm, and the macroporous specific surface area is 171 m$^2$/g. X-ray diffraction (XRD) shows that the multicomponent metal composite contains CuO, ZnO and the silicon-aluminum inorganic solid acid with MFI topology, and the crystal size of the metal oxide and the crystal size of the inorganic solid acid are 8-20 nm and 55-70 nm, respectively. Scanning electron microscopy (SEM) shows that the secondary particle size of the silicon-aluminum inorganic solid acid is 30-60 μm. High resolution transmission electron microscopy (HRTEM) shows that the crystal size of the multicomponent metal composite is 8-20 nm and the secondary particle size is 20-100 nm. NH$_3$ desorption peak temperature corresponding to medium strong acid is 408° C., and the amount of sites of the medium strong acid is 0.7 mol/kg.

Embodiment 9

The preparation process is substantially the same as that of embodiment 8, and the difference is that in the preparation process of the multicomponent metal composite, the predecessors are replaced with zinc nitrate hexahydrate, cobalt nitrate hexahydrate and aluminum nitrate nonahydrate, wherein the mass of zinc nitrate hexahydrate is 5.95 g, and the precursors are weighed according to the element molar ratio of Zn:Co:Al=1:0.01:1 and dissolved in 100 ml of deionized water. 14.3 g of ammonium carbonate is weighed and dissolved in 100 ml of deionized water.

The N$_2$ physical adsorption and desorption show that the catalyst has a hierarchical pore structure. The microporous specific surface area is 297 m$^2$/g with micropore size distribution of 3-4 Å, and the mesoporous specific surface area is 122 m$^2$/g with mesopore size distribution of 2-8 nm, and the macroporous specific surface area is 111 m$^2$/g. X-ray diffraction (XRD) shows that the multicomponent metal composite contains Co$_3$O$_4$, Co$_2$O$_3$, ZnO, Al$_2$O$_3$, ZnCo$_2$O$_4$ and the silicon-aluminum inorganic solid acid with CHA topology, and the crystal size of the metal oxide and the crystal size of the inorganic solid acid are 9-17 nm and 50-60 nm, respectively. Scanning electron microscopy (SEM) shows that the secondary particle size of the silicon-aluminum inorganic solid acid is 100-500 μm. High resolution transmission electron microscopy (HRTEM) shows that the crystal size of the multicomponent metal composite is 9-17 nm and the secondary particle size is 20-100 nm. NH$_3$ desorption peak temperature corresponding to medium strong acid is 363° C., and the amount of sites of the medium strong acid is 0.6 mol/kg.

In reference example 9, the preparation process is substantially the same as that of embodiment 8, and the difference is that in the preparation process of the multicomponent metal composite, ultransonic treatment is not used, aging is conducted at 90° C. for 0.5 h and the crystallization temperature is changed to 300° C., causing that the final catalyst cannot form a good crystal form and the finally obtained crystal size is less than 1 nm. The crystallization time is controlled as 1.5 h in the process of coating the inorganic solid acid. For the final catalyst, the microporous specific surface area is 148 m$^2$/g with micropore size distribution of 4-6 Å, and the mesoporous specific surface area is 27 m$^2$/g with mesopore size distribution of 20-47 nm, and the macroporous specific surface area is 7 m$^2$/g. The crystal size of the metal oxide is less than 1 nm and the secondary particle size is 10 nm-50 μm. The crystal size of the inorganic solid acid is 53-79 nm; the secondary particle size of the inorganic solid acid is 300-600 μm; NH$_3$ desorption peak temperature corresponding to medium strong acid is 410° C.; and the amount of sites of the medium strong acid is 0.05 mol/kg.

In reference example 10, the preparation process is substantially the same as that of embodiment 8, and the difference is that in the synthesis process of the multicomponent metal composite, the power of ultrasonic treatment is 0.5 W, aging is conducted at 30° C. for 3 days and the crystallization temperature is changed to 800° C., so that the crystal size of the final catalyst is greater than 30 nm. For the final catalyst, the microporous specific surface area is 757 m$^2$/g with micropore size distribution of 4-6 Å, and the mesoporous specific surface area is 147 m$^2$/g with mesopore size distribution of 8-14 nm, and the macroporous specific surface area is 150 m$^2$/g. The crystal size of the metal oxide is 30 nm-70 nm and the secondary particle size is 100 nm-50 μm. The crystal size of the inorganic solid acid is 80-120 nm and the secondary particle size of the inorganic solid acid is 200-800 μm. NH$_3$ desorption peak temperature corresponding to medium strong acid is 430° C., and the amount of sites of the medium strong acid is 4 mol/kg.

In embodiment 8, reference example 9 and reference example 10, under reaction conditions of 370° C., 2 MPa and volume space velocity of 7000 h$^{-1}$, reaction results are shown in the table below.

In embodiment 9, under reaction conditions of 400° C., 2.5 MPa and volume space velocity of 4000 h$^{-1}$, reaction results are shown in the table below.

| Catalyst | CO conversion % | CH$_x$ Selectivity % | CH$_4$ Selectivity % | C$_2$-C$_4$ Hydrocarbon Selectivity % | C$_2$=-C$_4$= Olefins Selectivity % | C$_{5+}$ Selectivity % |
|---|---|---|---|---|---|---|
| Embodiment 8 | 14.27 | 53.86 | 1.09 | 90.77 | 50.16 | 8.14 |
| Embodiment 9 | 17.40 | 57.00 | 8.4 | 76.68 | 63.97 | 16.89 |
| Reference Example 9 | 23.44 | 50.68 | 34.79 | 58.24 | 17.35 | 6.97 |
| Reference Example | 1.78 | 66.18 | 8.31 | 90.07 | 27.10 | 1.62 |

The crystal sizes of the multicomponent metal composite in the reference example 9 are very small, wherein many metals are present in the form of clusters of atoms formed by single atom or a few atoms, and the particle size is less than the preferred range described in the claims and also less than the crystal size range described in the claims. Although the CO conversion of the reference example 9 is increased, the methane selectivity is increased significantly by more than 30%, while the selectivity of the light olefins is decreased to be less than 20%. In the reference example 10, the crystal size of the multicomponent metal composite is larger than the upper limit of the crystal size range described in the claims. The excessively large particle size and the reduced specific surface area cause the insufficient capacity to actiare weighed. XRD shows that the multicomponent metal composite contains ZnO, CoO, Co, $ZnCo_2O_4$ and $CoTiO_3$. The metal Co content is 30% in all metal atoms according to the atomic number, exceeding 10% of the claims. The crystal size of the multicomponent metal composite is 8-40 nm and the secondary particle size is 30-120 nm.

Under reaction conditions of 400° C., 2 MPa and volume space velocity of 6000 $h^{-1}$, reaction results are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 10 | 7.83 | 59.64 | 2.99 | 89.17 | 57.40 | 7.84 |
| Reference Example | 35.78 | 78.01 | 27.76 | 21.67 | 17.18 | 50.57 | vate and convert the synthesis gas, resulting in very low CO conversion. Meanwhile, the hydrogenation is more serious, so the selectivity of the light olefins has declined. Therefore, the crystal size of the metal composite is critical to control of the catalytic performance.

Embodiment 10

The preparation process and method are substantially the same as those of embodiment 5, and the difference is that in the preparation process of the multicomponent metal composite, 17.33 g of zinc nitrate hexahydrate, 0.17 g of cobalt nitrate hexahydrate and 22.1 g of titanium chloride are respectively weighed and dissolved in 300 ml of deionized water; and 60.5 g of ammonium carbonate is weighed and dissolved in 300 ml of deionized water. The two groups of solutions are simultaneously added dropwise to the deionized water under ultrasonic agitation at constant temperature of 70° C. and precipitated, with an ultrasonic power of 5 W and a stirring rate of 500 rpm. Then, the precipitate is aged at 70° C. for 3 h and washed with 70° C. of deionized water to be neutral. Then, the precipitate is dried at 110° C. for 12 h and calcined at 500° C. for 1 h to prepare $ZnCo_{0.05}Ti_2$ composite oxide, wherein Co/Ti/Zn mole ratio is 0.05/2/1.

By this method, ZnCoTi oxide of different molar ratios can be obtained.

The $N_2$ physical adsorption and desorption show that the catalyst has a hierarchical pore structure. The microporous specific surface area is 251 $m^2/g$ with micropore size distribution of 4-5 Å, and the mesoporous specific surface area is 213 $m^2/g$ with mesopore size distribution of 4-13 nm, and the macroporous specific surface area is 216 $m^2/g$. X-ray diffraction (XRD) shows that the multicomponent metal composite contains ZnO, $Co_3O_4$, $TiO_2$, $ZnCo_2O_4$ and the silicon-aluminum inorganic solid acid with CHA topology, the crystal size of the metal oxide is 8-20 nm and the crystal size of the inorganic solid acid is 60-80 nm. Scanning electron microscopy (SEM) shows that the secondary particle size of the silicon-aluminum inorganic solid acid is 300-700 μm. High resolution transmission electron microscopy (HRTEM) shows that the crystal size of the multicomponent metal composite is 8-20 nm and the secondary particle size is 30-120 nm. $NH_3$ desorption peak temperature corresponding to medium strong acid is 377° C., and the amount of sites of the medium strong acid is 2 mol/kg.

In reference example 11, the preparation process is substantially the same as that of embodiment 10, and the difference is that the ratio of the metal elements in the multicomponent metal composite is changed to $Zn_{0.05}Co_3Ti_2$ to prepare the metal precursor solution according to the proportion for synthesis when the metal precursors For reference example 11, the $C_{5+}$ product of the reaction product accounts for more than 50% and methane accounts for more than 20% under the same conditions. Since the content of the metallic state Co in the catalyst is too high to be within the scope of the claims, the reaction tends to occur under the conventional Fischer-Tropsch synthesis path and the product is limited by the ASF distribution, resulting in low selectivity of light olefins and generating more long-carbon-chain hydrocarbons.

Embodiment 11

The preparation process and method are substantially the same as those of embodiment 8, and the difference is that the prepared silicon-phosphorus-aluminum inorganic solid acid with hierarchical pore structure is mixed with 10% of ammonium nitrate solution with a mass ratio of 1:500 and stirred at 80° C. for 8 h. After sucked and filtered and dried at room temperature, the resulting solid is mixed with 1% of copper nitrate solution with a mass ratio of 1:500 and stirred at 80° C. for 8 h. After sucked and filtered and dried at room temperature, the resulted mixture is dried in an oven at 110° C. for 14 h and calcined in air at 500° C. for 1 h to obtain Cu-ion exchanged multicomponent metal composite.

The preparation process of the multicomponent metal composite is different in that the preparation process of metal precursors includes weighing 5.95 g of zinc nitrate hexahydrate, weighing ammonium molybdate according to an element mole ratio of 1:1 and dissolving in 100 ml of deionized water. 11 g of ammonium carbonate is weighed and dissolved in 100 ml of deionized water.

The $N_2$ physical adsorption and desorption show that the catalyst has a hierarchical pore structure. The microporous specific surface area is 239 $m^2/g$ with micropore size distribution of 4-5 Å, and the mesoporous specific surface area is 271 $m^2/g$ with mesopore size distribution of 4-13 nm, and the macroporous specific surface area is 198 $m^2/g$. X-ray diffraction (XRD) shows that the multicomponent metal composite contains ZnO, CuO, $MoO_3$, $ZnMoO_4$ and the silicon-aluminum inorganic solid acid with CHA topology, the crystal size of the metal oxide is 12-26 nm and the crystal size of the inorganic solid acid is 60-90 nm. Scanning electron microscopy (SEM) shows that the secondary particle size of the silicon-aluminum inorganic solid acid is 300-700 μm. High resolution transmission electron microscopy (HRTEM) shows that the crystal size of the multicomponent metal composite is 12-26 nm and the secondary particle size is 30-120 nm. $NH_3$ desorption peak temperature corresponding to medium strong acid is 345° C., and the amount of sites of the medium strong acid is 0.5 mol/kg.

Embodiment 12

The preparation process is substantially the same as that of embodiment 11, and the difference is that metal elements in the multicomponent metal composite are replaced to ensure that the amount of replacing metal atoms is equal to the amount of replaced metal atoms. Ammonium molybdate is replaced with $VO_2NO_3$ when the metal precursor solution is prepared.

Embodiment 13

The preparation process is substantially the same as that of embodiment 11, and the difference is that metal elements in the multicomponent metal composite are replaced to ensure that the amount of replacing metal atoms is equal to the amount of replaced metal atoms. Ammonium molybdate is replaced with manganous nitrate when the metal precursor solution is prepared.

Under reaction conditions of 360° C., 0.8 MPa and volume space velocity of 3000 $h^{-1}$, reaction results are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 11 | 6.84 | 59.01 | 4.38 | 91.85 | 50.11 | 3.77 |
| Embodiment 12 | 6.72 | 60.16 | 4.39 | 83.58 | 53.07 | 12.03 |
| Embodiment 13 | 6.15 | 58.73 | 3.79 | 88.37 | 63.18 | 7.84 |

The difference of embodiments 11, 12 and 13 is that the metal element composition in the multicomponent metal composite is replaced from Mo to V and Mn. The selectivity of the light olefins is gradually increased. This is consistent with the preferred metal elements described in the claims.

Embodiment 14

The preparation process and method are substantially the same as those of embodiment 3, and the difference is that the preparation process and method of the silicon-phosphorus-aluminum inorganic solid acid with hierarchical pore structure are as follows: sodium silicate, boehmite, ethylenediamine and water are weighed according to the mass ratio of $SiO_2$:$Al_2O_3$:R:$H_2O$=300:15:30:100; after the materials are stirred in 250 ml of beaker at 50° C. and aged for 1 h, the materials are stirred at 30° C. for secondary aging; after stirred at 500 rpm for 72 h, the mixture is transferred to a hydrothermal reactor and crystallized in an oven at 150° C. for 47 h; the water bath is quenched to room temperature; centrifugal washing is repeated so that the pH of the supernatant is 7 at the end of washing; and after dried at 110° C. for 17 h, the precipitate is calcined in air at 550° C. for 3 h to obtain the silicon-aluminum inorganic solid acid with hierarchical pore structure.

The preparation process of the metal precursors of the multicomponent metal composite includes weighing 5.95 g of zinc nitrate hexahydrate, weighing palladium nitrate and zirconium nitrate pentahydrate according to an element mole ratio of Zn:Pd:Zr=1:0.01:1 and dissolving in 100 ml of deionized water. 11.3 g of ammonium carbonate is weighed and dissolved in 100 ml of deionized water.

The $N_2$ physical adsorption and desorption show that the catalyst has a hierarchical pore structure. The microporous specific surface area is 239 $m^2$/g with micropore size distribution of 4-5 Å, and the mesoporous specific surface area is 308 m2/g with mesopore size distribution of 4-13 nm, and the macroporous specific surface area is 161 $m^2$/g. X-ray diffraction (XRD) shows that the multicomponent metal composite contains ZnO, PdO, $ZrO_2$, $ZnZr_2O_4$ and the silicon-aluminum inorganic solid acid with CHA topology, the crystal size of the metal oxide is 12-22 nm and the crystal size of the inorganic solid acid is 60-90 nm. Scanning electron microscopy (SEM) shows that the secondary particle size of the silicon-aluminum inorganic solid acid is 300-700 μm. High resolution transmission electron microscopy (HRTEM) shows that the crystal size of the multicomponent metal composite is 12-22 nm and the secondary particle size is 40-120 nm. $NH_3$ desorption peak temperature corresponding to medium strong acid is 370° C., and the amount of sites of the medium strong acid is 1.6 mol/kg.

Embodiment 15

The preparation process is substantially the same as that of embodiment 14, and the difference is that the atomic ratio of the metal element Zn to the other elements is changed to 5:1 in the preparation process of the metal precursor of the multicomponent metal composite when the metal precursor solution is prepared.

In reference example 12, the preparation process is substantially the same as that of embodiment 14, and the difference is that the atomic ratio of the metal element Zn to the other elements is changed to 0.05:1 in the preparation process of the metal precursor of the multicomponent metal composite when the metal precursor solution is prepared.

Under reaction conditions of 380° C., 1.5 MPa and volume space velocity of 8000 $h^{-1}$, reaction results are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 14 | 8.19 | 54.45 | 4.07 | 66.18 | 55.85 | 29.75 |
| Embodiment 15 | 4.73 | 53.91 | 4.37 | 61.28 | 50.17 | 34.35 |
| Reference Example | 2.58 | 60.33 | 5.76 | 67.34 | 47.99 | 26.9 |

Compared with embodiment 14, reference example 12 changes the ratio of Zn to other elements; and the ratio in the reference 12 is not within the ratio range of claims. Therefore, the CO conversion is very low. Although the ratio in embodiment 15 is within the range of claims but not within the preferred range, the CO conversion is also low.

Embodiment 16

The preparation process and method of the silicon-phosphorus-aluminum inorganic solid acid with hierarchical pore structure are substantially the same as those of the embodiment 3, and the difference is that the obtained silicon-phosphorus-aluminum inorganic solid acid with hierarchical pore structure is placed in an ampoule of 10–2 Pa or more vacuum with constant temperature. The silicon-phosphorus-aluminum inorganic solid acid with hierarchical pore structure is heated at 5° C./min to a temperature of 420° C., then kept for 12 h. Then, the silicon-phosphorus-aluminum inorganic solid acid with hierarchical pore structure is sealed and transferred to the glove box with Ar atmosphere, then mixed with molybdenum chloride in accordance with the mass ratio of 1:0.1 and placed on both sides of the quartz ampoule. After put into 10–2 Pa vacuum, the quartz ampoule is enclosed so that the silicon-phosphorus-aluminum inorganic solid acid with hierarchical pore structure and the molybdenum chloride are enclosed together in the vacuum quartz ampoule. The quartz ampoule filled with the silicon-phosphorus-aluminum inorganic solid acid with hierarchical pore structure and the molybdenum chloride is placed in a tube furnace and heated at 10° C./min to 400° C., and held at 400° C. for 24 hours. Then, the quartz ampoule is dropped to room temperature and broken to obtain Mo—SiAlP with molybdenum oxide load of 1%.

The preparation process of the multicomponent metal composite is substantially the same as that of embodiment 5. The preparation process of the multicomponent metal composite is different in that the preparation process of metal precursors includes weighing 5.95 g of zinc nitrate hexahydrate, weighing ammonium molybdate according to an element mole ratio of 1:1 and dissolving in 100 ml of deionized water.

The $N_2$ physical adsorption and desorption show that the catalyst has a hierarchical pore structure. The microporous specific surface area is 533 $m^2/g$ with micropore size distribution of 4-5 Å, and the mesoporous specific surface area is 133 $m^2/g$ with mesopore size distribution of 3-8 nm, and the macroporous specific surface area is 118 $m^2/g$. X-ray diffraction (XRD) shows that the multicomponent metal composite contains $MoO_2$, ZnO, $Al_2O_3$, $ZnAl_2O_4$ and the silicon-aluminum inorganic solid acid with CHA topology, and the crystal size of the metal oxide and the crystal size of the inorganic solid acid are 7-12 nm and 50-60 nm, respectively. Scanning electron microscopy (SEM) shows that the secondary particle size of the silicon-aluminum inorganic solid acid is 100-500 μm. High resolution transmission electron microscopy (HRTEM) shows that the crystal size of the multicomponent metal composite is 7-12 nm and the secondary particle size is 20-100 nm. $NH_3$ desorption peak temperature corresponding to medium strong acid is 344° C., and the amount of sites of the medium strong acid is 2 mol/kg.

In reference example 13, the preparation process is substantially the same as that of embodiment 16, and the difference is that metal elements in the multicomponent metal composite are replaced to ensure that the amount of replacing metal atoms is equal to the amount of replaced metal atoms. Zinc nitrate is replaced with cerium nitrate when the metal precursor solution is prepared.

In reference example 14, the preparation process is substantially the same as that of embodiment 16, and the difference is that metal elements in the multicomponent metal composite are replaced to ensure that the amount of replacing metal atoms is equal to the amount of replaced metal atoms. Zinc nitrate is replaced with nanometer-sized titania sol when the metal precursor solution is prepared.

Under reaction conditions of 400° C., 3 MPa and volume space velocity of 4000 $h^{-1}$, reaction results are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 16 | 8.79 | 55.87 | 6.71 | 84.09 | 57.50 | 9.2 |
| Reference Example | <1 | — | — | — | — | — |
| Reference Example | <1 | — | — | — | — | — |

Reference examples 13 and 14 do not contain necessary elements of claims, so have hardly any catalytic activity.

Embodiment 17

The preparation process and method of the silicon-phosphorus-aluminum inorganic solid acid with hierarchical pore structure are the same as those of embodiment 5. The difference is that the preparation process of metal precursors includes weighing 1.73 g of zinc nitrate hexahydrate, weighing 1.49 g of gallium nitrate according to an element mole ratio of Zn:Ga=1:1 and dissolving in 100 ml of deionized water; and weighing according to an element mole ratio of Zn:Ti=1:1 and adding 4.65 g of $TiO_2$.

The $N_2$ physical adsorption and desorption show that the catalyst has a hierarchical pore structure. The microporous specific surface area is 289 $m^2/g$ with micropore size distribution of 4-5 Å, and the mesoporous specific surface area is 267 $m^2/g$ with mesopore size distribution of 5-13 nm, and the macroporous specific surface area is 161 $m^2/g$. X-ray diffraction (XRD) shows that the multicomponent metal composite contains ZnO, $Ga_2O_3$, $TiO_2$ and the silicon-aluminum inorganic solid acid with CHA topology, and the crystal size of the metal oxide and the crystal size of the inorganic solid acid are 13-20 nm and 60-80 nm, respectively. Scanning electron microscopy (SEM) shows that the secondary particle size of the silicon-aluminum inorganic solid acid is 300-700 μm. High resolution transmission electron microscopy (HRTEM) shows that the crystal size of the multicomponent metal composite is 13-20 nm and the secondary particle size is 30-120 nm. $NH_3$ desorption peak temperature corresponding to medium strong acid is 336° C., and the amount of sites of the medium strong acid is 0.47 mol/kg.

Embodiment 18

The preparation process and method are substantially the same as those of embodiment 3, and the difference is that the preparation of the silicon-phosphorus-aluminum inorganic solid acid with the hierarchical pore structure is as follows: 1.66 g of zinc nitrate hexahydrate, and corresponding amount of cobalt nitrate hexahydrate, 0.5 wt % of aqueous solution of manganese nitrate and titanium chloride according to the molar ratio of element: Zn:Co:Mn:Ti=1:0.05:1:1 are weighed to prepare a mixed solution A; and 15.41 g of ammonium carbonate is weighed and dissolved in 100 ml of water to prepare a solution B.

The $N_2$ physical adsorption and desorption show that the catalyst has a hierarchical pore structure. The microporous specific surface area is 316 $m^2/g$ with micropore size distribution of 4-5 Å, and the mesoporous specific surface area is 140 m²/g with mesopore size distribution of 3-9 nm, and the macroporous specific surface area is 99 m²/g. X-ray diffraction (XRD) shows that the multicomponent metal composite contains $Co_2O_3$, $Co_3O_4$, $MnO_2$, $TiO_2$, $ZnCo_2O_4$, $ZnMnO_3$ and the silicon-aluminum inorganic solid acid with CHA topology, the crystal size of the metal oxide is 9-18 nm and the crystal size of the inorganic solid acid is 50-60 nm. Scanning electron microscopy (SEM) shows that the secondary particle size of the silicon-aluminum inorganic solid acid is 100-500 μm. High resolution transmission electron microscopy (HRTEM) shows that the crystal size of the multicomponent metal composite is 9-18 nm and the secondary particle size is 20-100 nm. $NH_3$ desorption peak temperature corresponding to medium strong acid is 368° C., and the amount of sites of the medium strong acid is 2.3 mol/kg.

In embodiments 17 and 18, under reaction conditions of the catalyst: 400° C., 3.5 MPa and volume space velocity of 4000 h⁻¹, reaction results of embodiments 17 and 18 are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 17 | 7.42 | 58.19 | 2.59 | 89.99 | 57.18 | 7.42 |
| Embodiment 18 | 12.83 | 57.64 | 5.33 | 92.77 | 67.90 | 1.90 |

In embodiment 19, under reaction conditions of the catalyst in embodiment 17: 400° C., 3.5 MPa and volume space velocity of 1500 h⁻¹, results as reaction results of embodiment 19 are shown in the table below.

In embodiment 20, under reaction conditions of the catalyst in embodiment 18: 400° C., 3.5 MPa and volume space velocity of 1500 h⁻¹, results as reaction results of embodiment 20 are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 19 | 18.74 | 55.31 | 3.02 | 85.90 | 50.24 | 11.08 |
| Embodiment 20 | 30.18 | 58.44 | 5.96 | 89.67 | 63.70 | 4.37 |

In reference example 15, under reaction conditions of the catalyst in embodiment 17: 400° C., 3.5 MPa and volume space velocity of 300 h⁻¹, results as reaction results of reference example 15 are shown in the table below.

In reference example 16, under reaction conditions of the catalyst in embodiment 18: 400° C., 3.5 MPa and volume space velocity of 300 h⁻¹, results as reaction results of reference example 16 are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Reference Example 15 | 49.33 | 67.17 | 12.88 | 78.53 | 24.76 | 8.59 |
| Reference Example 16 | 63.87 | 69.44 | 15.02 | 75.24 | 13.87 | 9.74 |

Embodiments 17-20 and reference examples 15-16 change the reaction space velocity conditions without changing the catalyst. The space velocity of embodiments 17-18 is within the preferred range of the claims, and thus shows the highest selectivity of the light olefins, while the space velocity of embodiments 19-20 is not within the preferred range but is still within the scope of the claims, so the selectivity of light olefins is till high. However, in the reference examples 15-16, since the reaction space velocity is not within the scope of the claims, the selectivity of light olefins is very low.

Embodiment 21

A composite catalyst of the multicomponent metal composite and the silicon-aluminum inorganic solid acid with hierarchical pore structure is prepared by a chemical compounding method.

The multicomponent metal composite of CaMnAl and silicon-aluminum inorganic solid acid with hierarchical pore structure are taken as examples.

The raw materials of 30% silica sol (mass concentration), aluminum sulfate, calcium carbonate, N,N,N-trimethyl-adamantane ammonium hydroxide (R) and deionized water are weighed according to the oxide $SiO:Al_2O_3:Ca_2O:R_2O$: $H_2O$=40:1:7:5:900 (mass ratio); after mixing at room temperature and stirring at 60° C. and 200 rpm for 24 h, the mixture is transferred to a hydrothermal reactor and crystallized at 155° C. for 6 d. The mixture is naturally cooled to room temperature and transferred to a beaker to have a water bath at 70° C. Ammonium chloride is added according to a ratio of 100 ml of stock solution to 4 g of ammonium chloride, stirred at constant temperature for 3 h and subjected to centrifugal washing repeatedly so that the pH of the supernatant is 7 at the end of washing. After the precipitate is dried at 120° C. for 24 h, the precipitate is calcined in air at 650° C. for 3 h to obtain the silicon-aluminum inorganic solid acid with hierarchical pore structure.

The prepared silicon-aluminum inorganic solid acid with hierarchical pore structure is weighed; 1.49 g of manganese nitrate tetrahydrate is weighed; anhydrous calcium nitrate and aluminum nitrate nonahydrate are weighed according to an element mole ratio of Mn:Ca:Al=1:0.1:1 and dissolved into 100 ml of aqueous solution; CuZnAl is introduced into the silicon-aluminum inorganic solid acid with hierarchical pore structure through an immersion method, CaMnAl is introduced into the silicon-aluminum inorganic solid acid with hierarchical pore structure, dried in vacuum at room temperature and calcined in still air at 520° C. for 1.5 h to obtain $Ca_{0.1}Mn_1Al_1$/mesoSiAl. The loading capacity of the multicomponent metal composite is 50 wt %. According to the method, the metal components and the proportions thereof as well as the loading capacity of the multicomponent metal composite can be changed.

The $N_2$ physical adsorption and desorption show that the catalyst has a hierarchical pore structure. The total specific surface area is 565 m²/g, wherein the microporous specific surface area accounts for 27% of the total specific surface area and the micropore size distribution is 3-4 Å; the mesoporous specific surface area accounts for 57% of the total specific surface area and the mesopore size distribution is 6-12 nm; and the macroporous specific surface area accounts for 16% of the total specific surface area. X-ray diffraction (XRD) shows that the multicomponent metal composite contains CaO, $MnO_2$, $Al_2O_3$ and the silicon-aluminum inorganic solid acid with CHA topology, the crystal size of the metal oxide is 5-13 nm and the crystal size of the inorganic solid acid is 40-70 nm. Scanning electron microscopy (SEM) shows that the secondary particle size of the silicon-aluminum inorganic solid acid with hierarchical pore structure is 10-100 μm and the crystal size of the inorganic solid acid is 10-100 nm. High resolution transmission electron microscopy (HRTEM) shows that the crystal size of the multicomponent metal composite is 5-13 nm and the secondary particle size is 15-50 nm. $NH_3$ desorption peak temperature corresponding to medium strong acid is 370° C., and the amount of sites of the medium strong acid is 6 mol/kg.

Embodiment 22

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring time is controlled to 18 h, the mixture is transferred to a hydrothermal reactor and crystallized at 170° C. for 5 d.

For the obtained catalyst with hierarchical pore structure, the total specific surface area is 493 m²/g, wherein the microporous specific surface area accounts for 24% of the total specific surface area and the micropore size distribution is 3-4 Å; the mesoporous specific surface area accounts for 53% of the total specific surface area and the mesopore size distribution is 5-11 nm; and the macroporous specific surface area accounts for 23% of the total specific surface area. $NH_3$ desorption peak temperature corresponding to medium strong acid is 392° C., and the amount of sites of the medium strong acid is 3.1 mol/kg.

Embodiment 23

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring time is controlled to 3 h, the mixture is transferred to a hydrothermal reactor and crystallized at 165° C. for 5 d+10 h. Finally, the mixture is calcined at 620° C. for 80 min.

For the obtained catalyst with hierarchical pore structure, the total specific surface area is 408 m²/g, wherein the microporous specific surface area accounts for 16% of the total specific surface area and the micropore size distribution is 3-4 Å; the mesoporous specific surface area accounts for 53% of the total specific surface area and the mesopore size distribution is 5-13 nm; and the macroporous specific surface area accounts for 31% of the total specific surface area. $NH_3$ desorption peak temperature corresponding to medium strong acid is 389° C., and the amount of sites of the medium strong acid is 3.4 mol/kg.

Reference Example 17

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring temperature is controlled to 90° C. and stirring time is controlled to 1 h, the mixture is transferred to a hydrothermal reactor and crystallized at 215° C. for 7 d. Finally, the mixture is calcined at 550° C. for 4 h.

For the obtained catalyst with hierarchical pore structure, the total specific surface area is 390 m²/g, wherein the microporous specific surface area accounts for 66% of the total specific surface area and the micropore size distribution is 3-4 Å; the mesoporous specific surface area accounts for 26% of the total specific surface area and the mesopore size distribution is 2-4 nm; and the macroporous specific surface area accounts for 8% of the total specific surface area. $NH_3$ desorption peak temperature corresponding to medium strong acid is 403° C., and the amount of sites of the medium strong acid is 4.1 mol/kg.

Reference Example 18

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring temperature is controlled to 30° C. and the stirring time is controlled to 48 h, the mixture is transferred to a hydrothermal reactor and crystallized at 175° C. for 8 d. Finally, the mixture is calcined at 550° C. for 3 h.

For the obtained catalyst with hierarchical pore structure, the total specific surface area is 314 m²/g, wherein the microporous specific surface area accounts for 81% of the total specific surface area and the micropore size distribution is 3-4 Å; the mesoporous specific surface area accounts for 14% of the total specific surface area and the mesopore size distribution is 2-4 nm; and the macroporous specific surface area accounts for 5% of the total specific surface area. $NH_3$ desorption peak temperature corresponding to medium strong acid is 368° C., and the amount of sites of the medium strong acid is 0.9 mol/kg.

Under reaction conditions of 375° C., 3.7 MPa and volume space velocity of 6000 $h^{-1}$, reaction results are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 21 | 37.15 | 54.01 | 4.38 | 89.63 | 65.12 | 5.99 |
| Embodiment 22 | 33.68 | 58.39 | 2.75 | 89.99 | 70.50 | 7.26 |

| Catalyst | CO conversion % | CH$_x$ Selectivity % | CH$_4$ Selectivity % | C$_2$-C$_4$ Hydrocarbon Selectivity % | C$_2$=-C$_4$= Olefins Selectivity % | C$_{5+}$ Selectivity % |
|---|---|---|---|---|---|---|
| Embodiment 23 | 28.97 | 53.66 | 3.21 | 91.57 | 73.58 | 5.22 |
| Reference Example | 30.01 | 57.18 | 8.37 | 79.44 | 49.36 | 12.19 |
| Reference Example | 25.62 | 60.14 | 14.29 | 73.19 | 36.04 | 12.52 |

Compared with reference examples 17-18, embodiments 21-23 show better selectivity of light olefins because the content distribution of the three-level pore channels in reference examples 17-18 is not within the preferred range. However, embodiments 22 and 23 have a higher selectivity of light olefins than embodiment 21 because the macroporous content of embodiment 21 is not within the preferred range and the contents of the three-level pore channels of embodiments 22-23 are not only within the preferred range but also in the more preferred range, so embodiments 22-23 have excellent performance.

Embodiment 24

A composite catalyst of the multicomponent metal composite and the silicon-phosphorus-aluminum inorganic solid acid with hierarchical pore structure is prepared by a chemical compounding method.

The raw materials of white carbon black, aluminum nitrate, phosphoric acid, TEAOH(R) and deionized water are weighed according to the oxide MgO:SiO$_2$:Al$_2$O$_3$:H$_3$PO$_4$:R:H$_2$O=2:18:16:32:55:150 (mass ratio); after mixing at room temperature and stirring at 30° C. and 500 rpm for 10 h, the mixture is transferred to a hydrothermal reactor, crystallized at 200° C. for 29 h; and the mixture is continuously stirred at stirring speed of 100 rpm while crystallizing. The water bath is quenched to room temperature. Centrifugal washing is conducted repeatedly so that the pH of the supernatant is 7 at the end of washing. After the precipitate is dried at 110° C. for 24 h, the precipitate is calcined in air at 600° C. for 3 h to obtain the silicon-phosphorus-aluminum inorganic solid acid with hierarchical pore structure.

The silicon-phosphorus-aluminum inorganic solid acid with hierarchical pore structure is prepared by the above method. 1.54 g of manganese nitrate tetrahydrate is weighed; and calcium chloride and chromic nitrate nonahydrate are weighed according to a mole ratio of Mn:Ca:Cr=2:0.2:1 and dissolved into an aqueous solution to prepare a mixed solution A, wherein the mass ratio of the inorganic solid acid to Cr is 2:1. 6.3 g of ammonium carbonate is weighed and dissolved in 100 ml of water to prepare a solution B; the solution B is dropwise added at 50° C. to the mixed solution A stirred at a power of 7 W with tip ultransonic and a speed of 400 rpm; centrifugal washing is conducted so that the pH of the supernatant is 7 at the end of washing; the mixture is dried in the air at 110° C. and calcined in still air at 500° C. for 1 h to obtain Ca$_{0.2}$Mn$_2$Cr$_1$/MgSiPAl. Then, through Ca$_{0.2}$Mn$_2$Cr$_1$/MgSiPAl as a carrier, palladium diacetate Co(Ac)$_2$ is accurately weighed and dissolved in water, and introduced into Ca$_{0.2}$Mn$_2$Cr$_1$/MgSiPAl by impregnation, wherein the mole ratio of Co to Mn is 0.01. According to the method, the metal components and the proportions thereof as well as the loading capacity of the multicomponent metal composite can be changed.

The N$_2$ physical adsorption and desorption show that the catalyst has a hierarchical pore structure. Micropore size distribution is 2-4 Å; and mesopore size distribution is 4-8 nm. The total specific surface area is 416 m$^2$/g, wherein the microporous specific surface area accounts for 57%; the mesoporous specific surface area accounts for 21% of the total specific surface area; and the macroporous specific surface area accounts for 22% of the total specific surface area. The secondary particle size of the silicon-aluminum inorganic solid acid is 100-500 μm and the crystal size is 5-70 nm. High resolution transmission electron microscopy (HRTEM) shows that the crystal size of the multicomponent metal composite is 0.5-16 nm and the secondary particle size is 10-100 nm. NH$_3$ desorption peak temperature corresponding to medium strong acid is 371° C., and the amount of sites of the medium strong acid is 2.1 mol/kg.

Embodiment 25

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring temperature is controlled to 40° C. and the stirring time is controlled to 2 h, the mixture is transferred to a hydrothermal reactor and crystallized at 180° C. for 2 d. Finally, the mixture is calcined in flowing air at 550° C. for 4 h.

The N$_2$ physical adsorption and desorption show that the catalyst has a hierarchical pore structure. Micropore size distribution is 2-5 Å; and mesopore size distribution is 5-9 nm. The total specific surface area is 357 m$^2$/g, wherein the microporous specific surface area accounts for 43%; the mesoporous specific surface area accounts for 30% of the total specific surface area; and the macroporous specific surface area accounts for 27% of the total specific surface area. The secondary particle size of the silicon-aluminum inorganic solid acid is 50-150 μm and the crystal size is 20-80 nm. High resolution transmission electron microscopy (HRTEM) shows that the crystal size of the multicomponent metal composite is 1-13 nm and the secondary particle size is 10-80 nm. NH$_3$ desorption peak temperature corresponding to medium strong acid is 358° C., and the amount of sites of the medium strong acid is 1.9 mol/kg.

Embodiment 26

The preparation process of the catalyst is substantially the same as that of embodiment 21, and the difference is that in the preparation process of the silicon-aluminum inorganic solid acid with hierarchical pore structure, after precursors are weighed and mixed at room temperature and the stirring temperature is controlled 50° C. and the stirring time is controlled to 1 h, the mixture is transferred to a hydrothermal reactor and crystallized at 165° C. for 5 d+10 h. Finally, the mixture is calcined in still air at 620° C. for 2 h.

The N$_2$ physical adsorption and desorption show that the catalyst has a hierarchical pore structure. Micropore size distribution is 3-5 Å; and mesopore size distribution is 4-9 nm. The total specific surface area is 4415 m$^2$/g, wherein the microporous specific surface area accounts for 33%; the mesoporous specific surface area accounts for 35% of the total specific surface area; and the macroporous specific surface area accounts for 32% of the total specific surface area. The secondary particle size of the silicon-aluminum inorganic solid acid is 50-100 μm and the crystal size is 40-90 nm. High resolution transmission electron microscopy (HRTEM) shows that the crystal size of the multicomponent metal composite is 3-6 nm and the secondary particle size is 10-90 nm. $NH_3$ desorption peak temperature corresponding to medium strong acid is 397° C., and the amount of sites of the medium strong acid is 2.7 mol/kg.

Reference Example 19

The preparation process of the catalyst is substantially the same as that of embodiment 21, and the difference is that in the preparation process of the silicon-aluminum inorganic solid acid with hierarchical pore structure, raw materials are weighed according to oxide $MgO:SiO_2:Al_2O_3:H_3PO_4:R:H_2O:2:18:16:32:10:150$ (mass ratio) and precursors are mixed at room temperature. The crystallization temperature is controlled to 150° C. and the time is controlled to 24 h.

The $N_2$ physical adsorption and desorption show that the catalyst has a hierarchical pore structure. Micropore size distribution is 3-5 Å; and mesopore size distribution is 4-9 nm. The total specific surface area is 95 $m^2/g$, wherein the microporous specific surface area accounts for 11%; the mesoporous specific surface area accounts for 55% of the total specific surface area; and the macroporous specific surface area accounts for 34% of the total specific surface area. $NH_3$ desorption peak temperature corresponding to medium strong acid is 320° C., and the amount of sites of the medium strong acid is 0.02 mol/kg.

Reference Example 20

The preparation process of the catalyst is substantially the same as that of embodiment 21, and the difference is that in the preparation process of the silicon-aluminum inorganic solid acid with hierarchical pore structure, raw materials are weighed according to oxide $MgO:SiO_2:Al_2O_3:H_3PO_4:R:H_2O:2:18:16:32:80:150$ (mass ratio) and precursors are mixed at room temperature. The crystallization temperature is controlled to 180° C. and the time is controlled to 72 h. The calcination temperature is controlled to 550° C. and the time is controlled to 30 min in still air.

The $N_2$ physical adsorption and desorption show that the catalyst has a hierarchical pore structure. Micropore size distribution is 3-5 Å; and mesopore size distribution is 4-9 nm. The total specific surface area is 69 $m^2/g$, wherein the microporous specific surface area accounts for 14%; the mesoporous specific surface area accounts for 24% of the total specific surface area; and the macroporous specific surface area accounts for 62% of the total specific surface area. $NH_3$ desorption peak temperature corresponding to medium strong acid is 329° C., and the amount of sites of the medium strong acid is 0.03 mol/kg.

Under reaction conditions of 415° C., 3.0 MPa and volume space velocity of 5000 $h^{-1}$, reaction results are shown in the table below.

over, the content of the three-dimensional three-level pore channels and the content of the three-level pore channels formed as described by claims satisfy the preferred range of the claims, wherein embodiments 25-26 present more excellent performance in a more preferred range. In reference examples 19-20, although the three-dimensional three-level pore channels are formed, the ratio of the organic template agent to the water does not satisfy the scope of the claims, the organic template agent in reference example 19 is too little to form sufficient pore structures and the excess amount of the organic template agent in reference example 20 is too much and the calcination time does not satisfy the time range described in the claims. Therefore, the specific surface areas of reference examples 19-20 are lower than the range of the claims, causing that the CO conversion is very low and the selectivity of light olefins is also much lower than that of the catalyst of the present invention.

Embodiment 27

The preparation process of the catalyst is substantially the same as that of embodiment 5, and the difference is that metal elements in the multicomponent metal composite are replaced and in the preparation of the metal precursor solution, copper nitrate hexahydrate is replaced with sodium bicarbonate to ensure a ratio of replacing metal atoms to replaced metal atoms is 1:10; and cobalt nitrate hexahydrate is replaced with ferric ammonium citrate to ensure a ratio of replacing metal atoms to replaced metal atoms is 1:2.

Embodiment 28

The preparation process of the catalyst is substantially the same as that of embodiment 27, and the difference is that metal elements in the multicomponent metal composite are replaced and in the preparation of the metal precursor solution, sodium bicarbonate is replaced with basic magnesium carbonate to ensure a ratio of replacing metal atoms to replaced metal atoms is 1:1.

Embodiment 29

The preparation process of the catalyst is substantially the same as that of embodiment 27, and the difference is that metal elements in the multicomponent metal composite are replaced and in the preparation of the metal precursor solution, sodium bicarbonate is replaced with potassium nitrate to ensure a ratio of replacing metal atoms to replaced metal atoms is 1:1.

Embodiment 30

The preparation process of the catalyst is substantially the same as that of embodiment 27, and the difference is that metal elements in the multicomponent metal composite are replaced and in the preparation of the metal precursor solution, sodium bicarbonate is replaced with cesium nitrate to ensure a ratio of replacing metal atoms to replaced metal atoms is 1:1.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 24 | 27.15 | 60.04 | 2.34 | 92.49 | 65.34 | 5.17 |
| Embodiment 25 | 28.96 | 57.34 | 1.69 | 89.79 | 70.01 | 8.52 |
| Embodiment 26 | 31.48 | 52.29 | 3.08 | 91.06 | 75.48 | 5.86 |
| Reference Example | 5.04 | 56.80 | 17.23 | 55.98 | 37.44 | 26.79 |
| Reference Example | 2.67 | 45.18 | 23.84 | 46.10 | 33.27 | 30.06 |

For the crystals of embodiments 24-26, the crystal particles and the secondary particles sizes of the multicomponent metal composite and the silicon-aluminum inorganic solid acid satisfy the scope of the claims, and the specific surface areas thereof satisfy the scope of the claims. More- Embodiment 31

The preparation process of the catalyst is substantially the same as that of embodiment 27, and the difference is that metal elements in the multicomponent metal composite are replaced and in the preparation of the metal precursor solution, sodium bicarbonate is replaced with lanthanum nitrate to ensure a ratio of replacing metal atoms to replaced metal atoms is 1:1.

Embodiment 32

The preparation process of the catalyst is substantially the same as that of embodiment 5, and the difference is that metal elements in the multicomponent metal composite are replaced and in the preparation of the metal precursor solution, copper nitrate hexahydrate is replaced with 25 wt. % of manganous nitrate to ensure a ratio of replacing metal atoms to replaced metal atoms is 1:1; cobalt nitrate hexahydrate is replaced with ferric ammonium citrate to ensure a ratio of replacing metal atoms to replaced metal atoms is 1:2; and y-$Al_2O_3$ is replaced with gallium nitrate to ensure a ratio of replacing metal atoms to replaced metal atoms is 1:1.

Embodiment 33

The preparation process of the catalyst is substantially the same as that of embodiment 32, and the difference is that metal elements in the multicomponent metal composite are replaced and in the preparation of the metal precursor solution, gallium nitrate is replaced with germanium nitrate to ensure a ratio of replacing metal atoms to replaced metal atoms is 1:1.

Embodiment 34

The preparation process of the catalyst is substantially the same as that of embodiment 32, and the difference is that metal elements in the multicomponent metal composite are replaced and in the preparation of the metal precursor solution, gallium nitrate is replaced with zirconium nitrate to ensure a ratio of replacing metal atoms to replaced metal atoms is 1:1.

Embodiment 35

The preparation process of the catalyst is substantially the same as that of embodiment 32, and the difference is that metal elements in the multicomponent metal composite are replaced and in the preparation of the metal precursor solution, gallium nitrate is replaced with indium nitrate to ensure a ratio of replacing metal atoms to replaced metal atoms is 1:1.

Embodiments 36-40

The preparation process of the catalyst is substantially the same as those of embodiments 27-31, and the difference is that metal elements in the multicomponent metal composite are replaced and in the preparation of the metal precursor solution, zinc nitrate is replaced with 25 wt. % of manganous nitrate to ensure a ratio of replacing metal atoms to replaced metal atoms is 1:1.

Under reaction conditions of 400° C., 3.0 MPa and volume space velocity of 6000 $h^{-1}$, reaction results are shown in the table below.

Reference Example 21

As reference example 21, a mixture obtained by mechanically mixing a commercial Na-ZSM-5 molecular sieve with a composite oxide $Co_{0.1}Cr_3Zn_2$ prepared by a coprecipitation method is used as the catalyst. Under the same conditions, the selectivity of light alkane and light olefins is not greater than 20%' a great number of methane is generated; and the catalyst has poor stability and will be deactivated after 15 hours. Because the molecular sieve only contains the micropore structure and does not have the mesopore structure, carbon deposition generated in the reaction is very easy to block micropores, causing deactivation.

Reference Example 22

As reference example 22, the commercial CuZnAl catalyst used for methanol synthesis and a commercial MTO catalyst SAPO-34 without a hierarchical pore structure are mechanically mixed according to a mass ratio of 1:1 and reactions are carried out under the same conditions. Only alkanes are obtained, and olefins are hardly generated. Because the commercial SAPO-34 molecular sieve does not have the hierarchical pore structure as in claims, it is not beneficial for the mass transfer, causing excessive hydrogenation in the product and few olefins generated in the products.

Reference Example 23

By taking the carbon nanotube as a carrier and loading FeN nano-particles in a tube channel, the gathering and the growth of the nano-particles can be limited to avoid deactivation. Through promotion of K and Mn, $K_{0.4}Mn_{1.0}FeN@CNTs$ is obtained and light olefins can be generated selectively. Under conditions of 300° C., 5 bar, space velocity of 15000 $h^{-1}$ and $H_2/CO/Ar=47.5/47.4/5.1$, the CO conversion is 11.9% and the selectivity of $C_2^=-C_4^=$ is 43.6%. On the surface of the catalyst, surface carbon species generated through CO dissociation and $CH_x$ intermediate species generated through the reaction of the dissociated hydrogen atom are further coupled mutually on the surface, thereby generating hydrocarbons of different carbon chain lengths or generating alkanes through hydrogenation. Therefore, many products are generated and conform to ASF distribution.

Under reaction conditions of 400° C., 2 MPa and volume space velocity of 4000 $h^{-1}$, reaction results of reference examples 21 and 22 are shown in the table below.

Under reaction conditions of 300° C., 0.5 MPa and volume space velocity of 15000 $h^{-1}$, reaction results of the reference example 23 are shown in the table below.

| Catalyst | CO conversion % | $CH_x$ Selectivity % | $CH_4$ Selectivity % | $C_2$-$C_4$ Hydrocarbon Selectivity % | $C_2^=$-$C_4^=$ Olefins Selectivity % | $C_{5+}$ Selectivity % |
|---|---|---|---|---|---|---|
| Embodiment 27 | 15.74 | 56.23 | 6.17 | 86.81 | 65.93 | 7.02 |
| Embodiment 28 | 18.93 | 52.35 | 2.63 | 89.79 | 73.01 | 7.58 |
| Embodiment 29 | 14.28 | 56.09 | 9.08 | 85.13 | 76.28 | 5.79 |
| Embodiment 30 | 13.75 | 56.77 | 11.45 | 85.20 | 67.44 | 3.35 |
| Embodiment 31 | 17.53 | 60.18 | 1.68 | 86.30 | 73.17 | 12.02 |
| Embodiment 32 | 27.90 | 64.94 | 2.54 | 95.47 | 75.04 | 1.99 |
| Embodiment 33 | 28.06 | 58.14 | 1.78 | 90.79 | 70.01 | 7.43 |
| Embodiment 34 | 32.68 | 57.03 | 3.58 | 92.13 | 74.78 | 4.29 |
| Embodiment 35 | 33.67 | 56.93 | 6.28 | 86.98 | 66.12 | 6.74 |
| Embodiment 36 | 16.53 | 53.17 | 5.62 | 88.62 | 63.74 | 5.76 |
| Embodiment 37 | 19.02 | 52.35 | 2.63 | 89.79 | 73.01 | 7.58 |
| Embodiment 38 | 13.53 | 60.17 | 9.08 | 85.13 | 73.66 | 5.79 |
| Embodiment 39 | 16.02 | 62.37 | 15.62 | 75.20 | 60.03 | 9.18 |
| Embodiment 40 | 18.24 | 53.04 | 11.78 | 86.30 | 69.83 | 1.92 |

| Catalyst | CO conversion % | CH$_x$ Selectivity % | CH$_4$ Selectivity % | C$_2$-C$_4$ Hydrocarbon Selectivity % | C$_2$=-C$_4$= Olefins Selectivity % | C$_{5+}$ Selectivity % |
|---|---|---|---|---|---|---|
| Reference Example | 4.47 | 34.10 | 56.08 | 28.35 | 15.41 | 14.71 |
| Reference Example | 30.92 | 45.12 | 10.53 | 80.30 | 0.05 | 9.17 |
| Reference Example | 11.9 | 60.0 | 20.0 | 50.6 | 43.6 | 29.4 |

The selectivity of C$_2$-C$_4$ hydrocarbons of the products of the catalyst in embodiments 1-40 in the total hydrocarbon products can reach 60%-95%. The selectivity of the light olefins in the total hydrocarbon products is as high as 50%-85%. Because the metal composite surface of the catalyst has a low hydrogenation activity and low C—C coupling activity, the production of a large amount of methane is avoided and the methane selectivity and the selectivity of C$_{5+}$ long-carbon-chain hydrocarbon are very low and are less than 10%. The hierarchical pore structure of the inorganic solid acid avoids catalyst deactivation; the CO conversion after successive reaction for 100 hours is stable; and the product selectivity is stable.

Performance of catalysts in embodiments 1-40 are obviously better than that of traditional modified Fischer-Tropsch catalysts and catalysts obtained by mechanically mixing traditional MTO reaction catalysts and methanol synthesis catalysts. The reason is that: after the surface of the metal composite of the catalyst of the present invention is reduced and activated by hydrogen or carbon monoxide containing atmosphere, oxygen vacancy is formed in the surface structure, i.e., the metal is in a coordinative unsaturated state; CO can be catalyzed and activated efficiently to generate one or more than two species of intermediate species CH$_x$ (wherein x=1, 2 or 3); oxygen species on the surface and CO react to generate CO$_2$; the very active CH$_x$ species are combined with CO to generate CH$_x$CO, thereby avoiding generation of a large amount of methane; the selectivity of the methane and the selectivity of C$_{5+}$ long-carbon-chain hydrocarbon are very low, totally 5% to 10%. The simultaneously generated intermediate species are weakly adsorbed on the surface and can easily desorb from the surface and diffuse into pore channels of the inorganic solid acid, and can be further catalytically converted to generate light hydrocarbon over the catalytically acidic sites. The inorganic solid acid of the present invention has the hierarchical pore structure, thereby avoiding catalyst deactivation; CO conversion after continuous reaction for 100 hours is stable; and the product selectivity is stable. However, the traditional microporous molecular sieve catalyst does not have the hierarchical pore structure, and is very easy to be blocked by the intermediate species generated through the reaction, causing quick catalyst deactivation and being not beneficial for the mass transfer; direct mixing leads to formation of only alkanes, and olefins are hardly produced. In contrast, the catalyst with Fe as major component still follows the Fischer-Tropsch reaction mechanism, i.e., CO is dissociated and adsorbed on the catalyst surface to generate surface carbon and surface oxygen. The surface oxygen reacts with adsorbed hydrogen to generate water. The surface carbon reacts with the surface hydrogen to generate CH$_x$. The CH$_x$ is strongly adsorbed on the surface, and goes through surface polymerization reaction on the surfaces to generate longer-carbon-chain. Hydrocarbons with different carbon chain lengths are formed depending on the properties of the catalyst surface and desorb into the gas phase as products.

The catalyst provided by the present invention is a composite material and includes effective components of the multicomponent metal composites and the inorganic solid acid with hierarchical pore structures. The synthesis gas can be catalyzed to convert to C$_2$-C$_4$ light hydrocarbons. The single pass CO conversion is 10%-60%. The selectivity of light hydrocarbons in all hydrocarbon products can be up to 60%-95%, wherein the selectivity of light olefins (C$_2$=-C$_4$=) is 50%-85%. The method has the characteristics of simple process flow, less operation units and low capital investment, and has important application prospects.

We claim:

1. A catalyst, comprising a multicomponent metal composite dispersed on surfaces or in pore channels of an inorganic solid acid,
    wherein the multicomponent metal composite comprises two or more metals, and a weight percentage of the multicomponent metal composite in the catalyst is 10 wt % to 75 wt %,
    wherein the inorganic solid acid has a hierarchial pore structure and comprises micropores having pore diameters of less than 2 nm, mesopores having pore diameters of 2 nm to 50 nm, and macropores having pore diameters of larger than 50 nm,
    wherein the inorganic solid acid support has a BET surface area of 100-1200 m$^2$/g, and a pore volume of 0.25-0.80 ml/g, determined by N2 physical adsorption, and
    wherein 16-68% of the BET surface area is attributed to the micropores, 17-57% of the BET surface area is attributed to the mesopores, and 10-32% of the BET surface area is attributed to the macropores.

2. The catalyst according to claim 1, wherein each of the two or more metals in the multicomponent metal composite is in a form independently selected from the group consisting of a metal oxide, an elemental metal, a metal carbide, a metal nitride, and a metal inorganic salt, and
    wherein the two more metal elements comprises one or more necessary metal element and one or more other element, wherein the one or more necessary metal element is selected from the group consisting of Zn, Co, Cr, and Mn,
    wherein a molar ratio of the one or more necessary element to the one or more other element is (0.1-5.0):1,
    wherein the metal inorganic acid salt comprises a cation and an anion, wherein the metal in the cation is selected from the group consisting of Li, Na, Mg, Al, K, Ca, Sr, Ba, Ti, V, Cr, Mn, Fe, Co, Cu, Zn, Ga, Ge, Zr, Mo, Pd, Ag, Cd, Sn, Cs, and Ce, and the anion is selected from the group consisting of ZnO$_2^{2-}$, Al$_2$O$_4^{2-}$, SiO$_3^{2-}$, SiO$_4^{4-}$, TiO$_3^{2-}$, TiO$_3^{3-}$, VO$_3^-$, VO$_3^{2-}$, CrO$_4^{2-}$, Cr$_2$O$_4^{2-}$, Mn$_2$O$_4^{2-}$, Fe$_2$O$_4^{2-}$, Co$_2$O$_4^{2-}$, Ni$_2$O$_4^{2-}$, Fe(CN)$_6^{3-}$, Fe(CN)$_6^{4-}$, MoO$_4^{2-}$, TiO$_3^{2-}$, ZrO$_3^{2-}$, CeO$_3^{2-}$, Ga$_2$O$_4^{2-}$, In$_2$O$_4^{2-}$, GeO$_3$O$^{2-}$, GeO$_4^{4-}$, and SrO$_3^{4-}$ and
    wherein the metal in the cation and the metal in the anion are not the same.

3. The catalyst according to claim 2, wherein
    the multicomponent metal composite comprises secondary particles of 10 nm-200 μm in size and having mesopores of 2-20 nm in diameter, and wherein the secondary particles comprises crystal particles of 0.5-20 nm aggregated together.

4. The catalyst according to claim 1, wherein the inorganic solid acid is composed of Si, O, and H, is composed of Si, Al, O, and H, is composed of Si, Al, P, O, and H, is composed of Ti, Si, O, and H, is composed of Zr, Si, O, and H, is composed of Ge, Si, O and H, or is composed of Ge, Al, P, O and H.

5. The catalyst according to claim 1, wherein the inorganic solid acid comprises weak acid sites, medium strong acid sites, and strong acid sites defined according to $NH_3$-TPD (temperature programmed desorption),
wherein the weak acid sites have a deposition temperature of $NH_3$ lower than 275° C.,
the medium strong acid sites have a deposition temperature of $NH_3$ between 275° C. and 500° C., and
the strong acid sites have a deposition temperature of $NH_3$ higher than 500° C.,
wherein an amount of the medium strong acid sites is 0.06-10 mol/kg.

6. A method for preparing light olefins directly from a synthesis gas using the catalyst of claim 1, comprising:
contacting the synthesis gas with the catalyst of claim 1 in a reactor, wherein a volume ratio of $H_2$/CO in the synthesis gas is 0.5-4.

7. The method according to claim 6, further comprising pretreating the catalyst in a gas mixture at 250-600° C. under a pressure of 0.1-3.0 MPa at a space velocity of the gas mixture of is 500-5000 $h^{-1}$,
wherein the gas mixture is a mixture of hydrogen and carbon monoxide at a volume ratio of $H_2$/CO between 0.5-4;
or a mixture of hydrogen and inert gas selected from the group consisting of nitrogen, helium, argon, neon, or mixtures thereof, and a volume percentage of hydrogen in the mixture is 5-100%;
or a mixture of carbon monoxide and inert gas selected from the group consisting of nitrogen, helium, argon, neon, or mixtures thereof, and a volume percentage of carbon monoxide in the mixture is 5-100%.

8. The method according to claim 6, wherein the synthesis gas comprises $H_2$, CO, and one or more selected from the group consisting of an inert gas and an non-inert gas,
wherein the inert gas is one or more selected from the group consisting of nitrogen, helium, argon, and neon,
wherein the non-inert gas is one or more selected from the group consisting of carbon dioxide, steam, methanol, and ethanol, and
wherein the volume percentage of the inert gas in the synthesis gas is less than 10% and the volume percentage of the non-inert gas in the synthesis gas is less than 50%.

9. The method according to claim 6, wherein the reactor is a fluidized bed, a moving bed, or a fixed bed, wherein a reaction temperature is 300-500° C., and a space velocity of the synthesis gas is 500-10000 $h^{-1}$.

10. The catalyst according to claim 2, wherein the necessary metal element is Zn, and the other element is one or more selected from the group consisting of Li, Na, Mg, Al, K, Ca, Sr, Ba, Ti, V, Cr, Mn, Fe, Co, Cu, Ga, Ge, Zr, Mo, Pd, Ag, Cd, In, Sn, Cs, La, and Ce.

11. The catalyst according to claim 10, wherein the other element is one or more selected from the group consisting of Al, Ti, Cr, Mn, Co, Cu, Pd, and Ce.

12. The catalyst according to claim 2, wherein the necessary metal element is Co, and the other element is one or more selected from the group consisting of Li, Na, Mg, Al, K, Ca, Sr, Ba, Ti, V, Cr, Mn, Fe, Cu, Zn, Ga, Ge, Zr, Mo, Pd, Ag, Cd, In, Sn, Cs, La, and Ce.

13. The catalyst according to claim 12, wherein the other element is one or more selected from the group consisting of Al, Ti, Cr, Mn, Cu, Zn, Pd, and Ce.

14. The catalyst according to claim 2, wherein the necessary metal element is Cr, and the other element is one or more selected from the group consisting of Li, Na, Mg, Al, K, Ca, Sr, Ba, Ti, V, Mn, Fe, Co, Cu, Zn, Ga, Ge, Zr, Mo, Pd, Ag, Cd, In, Sn, Cs, La, and Ce.

15. The catalyst according to claim 14, wherein the other element is one or more selected from the group consisting of Al, Ti, Mn, Co, Cu, Zn, Pd, and Ce.

16. The catalyst according to claim 2, wherein the necessary metal element is Mn, and the other element is one or more selected from the group consisting of Li, Na, Mg, Al, K, Ca, Sr, Ba, Ti, Cr, Fe, Co, Cu, Zn, Ga, Ge, Zr, Mo, Pd, Ag, Cd, In, Sn, Cs, La, and Ce.

17. The catalyst according to claim 16, wherein the other element is one or more selected from the group consisting of Al, Ti, Cr, Co, Cu, Zn, Pd, and Ce.

18. A catalyst, comprising a multicomponent metal composite dispersed on surfaces or in pore channels of an inorganic solid acid,
wherein the muiticomponent metal composite comprises two or more metals, and a weight percentage of the multicomponent metal composite in the catalyst is 10 wt % to 75 wt %,
wherein the inorganic solid add has a hierarchical pore structure and comprises micropores having pore diameters of less than 2 nm, mesopores having pore diameters of 2 nm to 50 nm, and macropores having pore diameters of larger than 50 nm, wherein the inorganic solid add has a BET surface area of 100-1200 $m^2$/g, and a pore volume of 0.25-0.80 ml/g, determined by N2 physical adsorption, and
wherein 10-65% of the BET surface area is attributed to the micropores, 20-75% of the BET surface area is attributed to the mesopores, and 15-70% of the BET surface area is attributed to the micropores macropores.

19. The catalyst according to claim 18, wherein the inorganic solid acid has a BET surface area of 100-1200 $m^2$/g, and a pore volume of 0.25-0.80 ml/g, determined by N2 physical adsorption, and
wherein 10-50% of the BET surface area is attributed to micropores, 30-70% of the BET surface area is attributed to mesopores, and 20-60% of the BET surface is attributed to macropores.

* * * * *